(12) United States Patent
Kai et al.

(10) Patent No.: US 8,062,769 B2
(45) Date of Patent: Nov. 22, 2011

(54) INDOLOCARBAZOLE COMPOUND FOR USE IN ORGANIC ELECTROLUMINESCENT DEVICE AND ORGANIC ELECTROLUMINESCENT DEVICE

(75) Inventors: Takahiro Kai, Kitakyushu (JP); Masaki Komori, Kitakyushu (JP); Toshihiro Yamamoto, Kitakyushu (JP)

(73) Assignee: Nippon Steel Chemical Co., Ltd., Tokyo (JP)

( * ) Notice: Subject to any disclaimer, the term of this patent is extended or adjusted under 35 U.S.C. 154(b) by 253 days.

(21) Appl. No.: 12/439,787

(22) PCT Filed: Nov. 8, 2007

(86) PCT No.: PCT/JP2007/071728
§ 371 (c)(1),
(2), (4) Date: Mar. 30, 2009

(87) PCT Pub. No.: WO2008/056746
PCT Pub. Date: May 15, 2008

(65) Prior Publication Data
US 2010/0187977 A1    Jul. 29, 2010

(30) Foreign Application Priority Data
Nov. 9, 2006   (JP) .................................. 2006-303733

(51) Int. Cl.
H01J 1/63      (2006.01)
C07D 487/04    (2006.01)
(52) U.S. Cl. ...... 428/690; 428/917; 313/504; 546/276.7
(58) Field of Classification Search .......... None
See application file for complete search history.

(56) References Cited

U.S. PATENT DOCUMENTS
5,942,340 A  *  8/1999  Hu et al. ................ 428/690

FOREIGN PATENT DOCUMENTS
| JP | 11-162650 A | 6/1999 |
| JP | 11-167215 A | 6/1999 |
| JP | 11-176578 A | 7/1999 |
| JP | 2001-313178 A | 11/2001 |
| JP | 2002-305083 A | 10/2002 |
| JP | 2002-352957 A | 12/2002 |
| JP | 2003-515897 A | 5/2003 |
| JP | 2004-204234 A | 7/2004 |
| JP | 2006-183048 A | 7/2006 |
| WO | WO-2007/063754 A1 | 6/2007 |

OTHER PUBLICATIONS

The International Preliminary Report on Patentability and Written Opinion for International Appl. No. PCT/JP2007/071728, mailed Jun. 4, 2009.

Pindur et al., "Indolo[3,2-b]carbazol: Reaktionsprodukt der Umsetzung von 3,3'—Bisindolylmethan mit Orthoameisensäuretriethylester", Archiv der Pharmzaie, vol. 320, p. 280-282, Mar. 1987.

Hu et al., "An Efficient and General Synthesis of Indolo[2,3-a]carbazoles Using the Fischer Indole Synthesis", Synlett, No. 1, p. 0042-0048, 2005.

* cited by examiner

Primary Examiner — Dawn L Garrett
Assistant Examiner — Andrew K Bohaty
(74) Attorney, Agent, or Firm — Birch, Stewart, Kolasch & Birch, LLP

(57) ABSTRACT

Provided is an organic electroluminescent device (organic EL device) that is improved in luminous efficiency, fully secured of driving stability, and simply constructed. The EL device has a light-emitting layer disposed between an anode and a cathode stacked one upon another on a substrate and the light-emitting layer comprises a phosphorescent dopant and an indolocarbazole derivative as a host material. Examples of the indolocarbazole compounds include a compound represented by the following formula (2) or (3), wherein X is N or CH, at least one of Xs is N, and $Ar_1$ to $Ar_3$ each is a substituted or unsubstituted aromatic group.

10 Claims, 1 Drawing Sheet (2)

(3)

US 8,062,769 B2

INDOLOCARBAZOLE COMPOUND FOR USE IN ORGANIC ELECTROLUMINESCENT DEVICE AND ORGANIC ELECTROLUMINESCENT DEVICE

FIELD OF TECHNOLOGY

This invention relates to a novel compound for use in an organic electroluminescent device and to an organic electroluminescent device (hereinafter referred to as organic EL device) and, more particularly, relates to an organic EL device which uses a phosphorescent dopant and a host compound having a specific structure together to emit light of high luminance.

BACKGROUND TECHNOLOGY

An organic EL device of the simplest structure is generally constituted of a light-emitting layer sandwiched between a pair of counter electrodes and utilizes the following light-emitting phenomenon. Upon application of an electrical field between the electrodes, electrons are injected from the cathode and holes are injected from the anode and they recombine in the light-emitting layer; the energy level after recombination goes back from the conduction band to the valence band with release of energy in the form of light.

In recent years, organic thin films have been used in the development of EL devices. In particular, in an effort to enhance the luminous efficiency, the kind of electrodes has been optimized for the purpose of improving the efficiency of injecting carriers from the electrodes and a device has been developed in which a hole-transporting layer of an aromatic diamine and a light-emitting layer of 8-hydroxyquinoline aluminum complex (hereinafter referred to as Alq3) are disposed in thin film between the electrodes. This device has brought about a marked improvement in the luminous efficiency over the conventional devices utilizing single crystals of anthracene and the like and thereafter the developmental works of organic EL devices have been focused on commercial application to high-performance flat panels featuring self-luminescence and high-speed response.

In another effort to enhance the luminous efficiency of the device, the use of phosphorescence in place of fluorescence is investigated. The aforementioned device comprising a hole-transporting layer of an aromatic diamine and a light-emitting layer of Alq3 and many other devices utilize fluorescence. The use of phosphorescence, that is, emission of light from the excited triplet state is expected to enhance the luminous efficiency approximately three times that of the conventional devices utilizing fluorescence (emission of light from the excited singlet state). To achieve this objective, coumarin derivatives and benzophenone derivatives have been investigated as a material for the light-emitting layer, but they merely produced luminance at an extremely low level. Thereafter, europium complexes were tried to utilize the excited triplet state, but failed to emit light at high efficiency.

Patent document 1: JP2003-515897 A
Patent document 2: JP2001-313178 A
Patent document 3: JP2002-305083 A
Patent document 4: JP2002-352957 A
Patent document 5: JPH11-162650 A
Patent document 6: JPH11-176578 A A large number of phosphorescent dopants useful for the light-emitting layer of an organic EL device are disclosed in the patent document 1 and elsewhere. A typical example is tris(2-phenylpyridine)iridium complex (hereinafter referred to as Ir(ppy)3).

A carbazole compound or CBP described in the patent document 2 is proposed as a host material for use in the light-emitting layer of an organic EL device. Since CBP has a special property of facilitating the flow of holes and obstructing the flow of electrons, the use of CBP as a host material for Ir(ppy)3 that is a green light-emitting phosphorescent material destroys the balanced injection of charges thereby causing excess holes to flow out to the side of the electron-transporting layer and, as a result, the luminous efficiency from Ir(ppy)3 drops.

As a means to solve the aforementioned problems, a hole-blocking layer may be disposed between the light-emitting layer and the electron-transporting layer, for example, in the manner described in the patent document 3. The hole-blocking layer accumulates holes efficiently in the light-emitting layer thereby improving the probability of recombination of holes and electrons in the light-emitting layer and enhancing the luminous efficiency. Examples of the hole-blocking materials currently in general use include 2,9-dimethyl-4,7-diphenyl-1,10-phenanthroline (hereinafter referred to as BCP) and p-phenylphenolato-bis(2-methyl-8-quinolinolato-N1,O8)aluminum (hereinafter referred to as BAlq). The hole-blocking layer can prevent electrons and holes from recombining in the electron-transporting layer. However, BCP lacks reliability as a hole-blocking material as it tends to crystallize easily even at room temperature and a device comprising BCP shows an extremely short service life. On the other hand, BAlq is reported to have a Tg of approximately 100° C. and help to show a relatively long service life when incorporated in a device; however, BAlq does not have a sufficient hole-blocking ability and the luminous efficiency from Ir(ppy)3 drops.

Now, 3-phenyl-4-(1'-naphthyl)-5-phenyl-1,2,4-triazole (hereinafter referred to as TAZ) described in the patent document 4 is also proposed as a host material for a phosphorescent organic EL device; however, TAZ has a property of facilitating the flow of electrons and obstructing the flow of holes and displaces the light-emitting range toward the side of the hole-transporting layer. Hence, it is conceivable that the luminous efficiency from Ir(ppy)3 may drop depending upon the compatibility of Ir(ppy)3 with the material of choice for the hole-transporting layer. For example, 4,4'-bis[N-(1-naphthyl)-N-phenylamino]biphenyl (hereinafter referred to as NPB) is a material most widely used in the hole-transporting layer on account of its excellent performance, high reliability, and long service life; however, it is poorly compatible with Ir(ppy)3 and energy transition occurs from Ir(ppy)3 to NPB to lower the luminous efficiency.

The indolocarbazole compounds disclosed in the patent documents 5 and 6 are recommended for use as hole-transporting materials and their stability is admired. However, these documents do not teach the use as a phosphorescent host material. Moreover, the disclosed compounds differ in structure from those to be provided by this invention.

DISCLOSURE OF THE INVENTION

Problems to be Solved by the Invention

In applications of organic EL devices to display devices such as flat panel displays, it is necessary to improve the luminous efficiency of the device and, at the same time, to fully secure the driving stability of the device. Under the aforementioned circumstances, an object of this invention is to provide an organic EL device that performs at high efficiency with good driving stability and can be put to practical use and to provide a compound suitable therefor.

Means to Solve the Problems

The inventors have conducted intensive studies, found that the aforementioned problems can be solved by the use of a compound of specified structure in an organic EL device, and completed this invention.

Accordingly, this invention provides an organic EL device that performs at high efficiency with good driving stability and is practically useful by the use of a compound having a specified indolocarbazole skeleton.

A compound for use in an organic electroluminescent device according to this invention is represented by the following general formula (1):

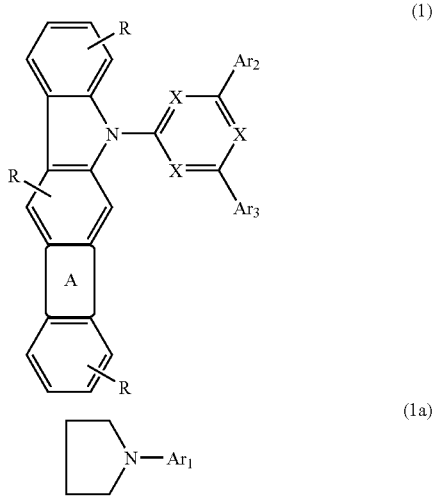

(1)

(1a)

wherein, ring A is a heterocyclic ring represented by formula (1a) and is condensed with the adjacent rings at arbitrary positions; X is N or CH and at least one of Xs is a nitrogen atom; $Ar_1$ to $Ar_3$ each is independently a substituted or unsubstituted non-condensed aromatic hydrocarbon group or a substituted or unsubstituted non-condensed aromatic heterocyclic group and $Ar_2$ and $Ar_3$ each may form a condensed ring with the X-containing ring; R is hydrogen or a monovalent substituent.

The compounds for use in an organic electroluminescent device represented by general formula (1) include the compounds represented by the following general formula (2) or (3):

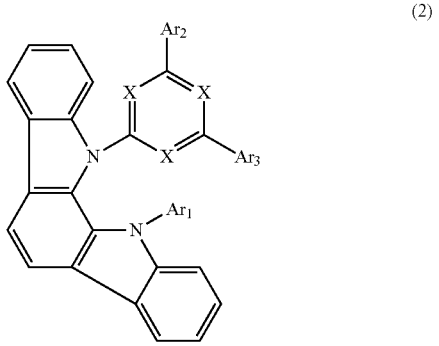

(2)

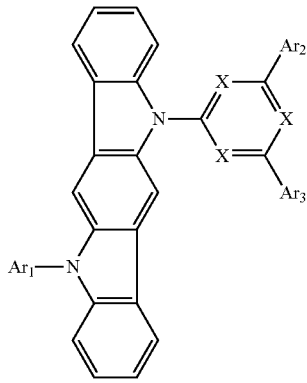

(3)

X and $Ar_1$ to $Ar_3$ in general formulas (2) and (3) have the same meaning as X and $Ar_1$ to $Ar_3$ in general formula (1).

This invention further relates to an organic electroluminescent device having an organic layer comprising the aforementioned compound for use in an organic electroluminescent device. Advantageously, the organic electroluminescent device has a light-emitting layer disposed between an anode and a cathode stacked one upon another on a substrate and the said light-emitting layer comprises a phosphorescent dopant and a compound for use in an organic electroluminescent device represented by the aforementioned general formula (1), (2), or (3) as a host material.

EXPLANATION OF SYMBOLS

Figure 1:
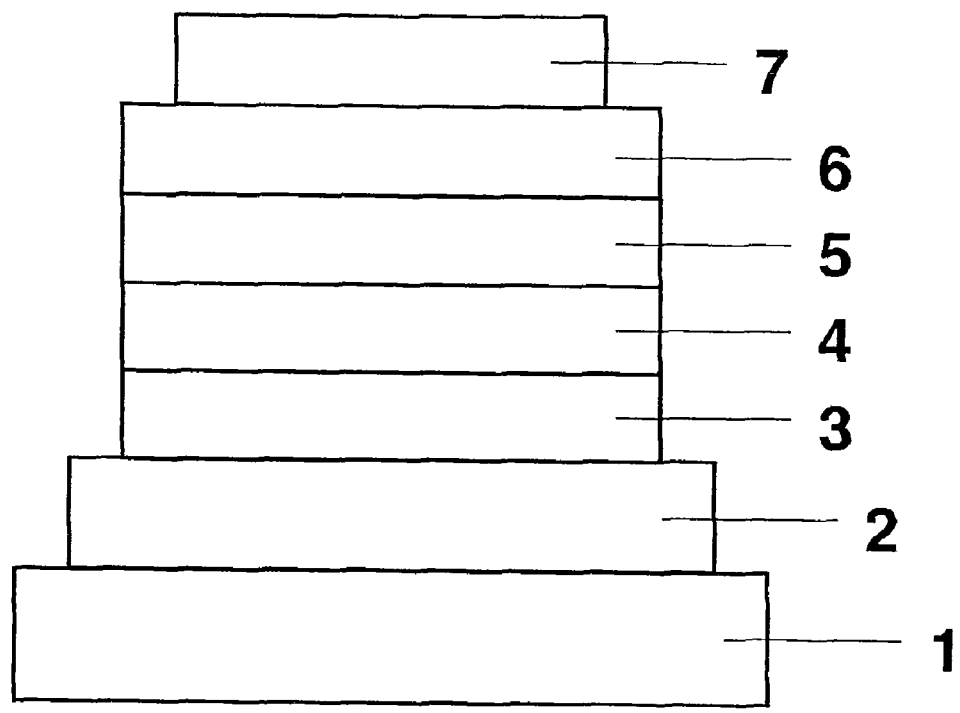
FIG. 1 schematically shows the cross section of an example of organic EL device.

1 substrate, 2 anode, 3 hole-injecting layer, 4 hole-transporting layer, 5 light-emitting layer, 6 electron-transporting layer, 7 cathode

PREFERRED EMBODIMENTS OF THE INVENTION

The mode of reduction to practice of this invention will be described in detail below.

A compound for use in an organic EL device according to this invention is represented by the aforementioned general formula (1). Any of the compounds represented by general formula (1) has a skeleton formed by the condensation of a carbazole ring with an indole ring. A ring containing 3 Xs (referred to as an X-containing ring) is linked to the N atom of the carbazole ring and R and $Ar_1$ to $Ar_3$ are suitably linked to individual rings. The indole ring is formed by the condensation of ring A with a benzene ring.

In general formula (1), ring A denotes a heterocyclic ring represented by formula (1) and it is condensed with the adjacent rings. Here, the heterocyclic ring represented by formula (1a) may be condensed with the adjacent carbazole ring at an arbitrary position. Concretely, the condensation may occur at the 2,3-, 3,4-, or 4,5-position.

In the X-containing ring linked to the N atom of the carbazole ring, X is CH or N and at least one of Xs is a nitrogen atom. Preferably, one, two, or three of Xs are nitrogen atoms.

The groups $Ar_1$ to $Ar_3$ each is a substituted or unsubstituted non-condensed aromatic hydrocarbon group or a substituted or unsubstituted non-condensed aromatic heterocyclic group. Preferable unsubstituted aromatic hydrocarbon groups include a phenyl group, a biphenylyl group, a terphenylyl group, and quaterphenylyl group. Preferable unsubstituted aromatic heterocyclic groups include a pyridyl group, pyrimidyl group, a triazyl group, an imidazolyl group, and a thienyl group.

When these aromatic hydrocarbon groups or aromatic heterocyclic groups have substituents, preferable examples of such substituents include alkyl groups of 1 to 4 carbon atoms, alkoxyl groups of 1 to 4 carbon atoms, a phenoxyl group, alkylthio groups, substituted amino groups, and an acetyl group. The examples further include aromatic hydrocarbon groups of 5 to 18 carbon atoms and aromatic heterocyclic groups of 3 to 17 carbon atoms.

The group $Ar_2$ or $Ar_3$ may condense with the X-containing ring to form a condensed ring.

In the case where the X-containing ring linked to the N atom of the carbazole ring is a pyridine ring in general formula (1), one of three Xs is a nitrogen atom and preferably located in the p-position to the carbon atom linked to the N atom in the carbazole ring. Where the X-containing ring is a pyrimidine ring, two of three Xs are nitrogen atoms and preferably located at both of the o-positions.

The group R is hydrogen or a monovalent substituent. To be specific, R is independently hydrogen, an alkyl group, an aralkyl group, an alkenyl group, an alkynyl group, a cyano group, a dialkylamino group, a diarylamino group, a diaralkylamino group, an amino group, a nitro group, an acyl group, an alkoxycarbonyl group, a carboxyl group, an alkoxyl group, an alkylsulfonyl group, a haloalkyl group, a hydroxyl group, an amide group, a substituted or unsubstituted aromatic hydrocarbon group, or a substituted or unsubstituted aromatic heterocyclic group. Preferable monovalent substituents include alkyl groups of 1 to 4 carbon atoms, alkoxyl groups of 1 to 4 carbon atoms, a phenoxyl group, alkylthio groups, substituted amino groups, and an acetyl group. They further include substituted or unsubstituted aromatic hydrocarbon groups of 5 to 18 carbon atoms and substituted or unsubstituted aromatic heterocyclic groups of 3 to 17 carbon atoms.

Of the compounds represented by the aforementioned general formula (1), the compounds represented by the aforementioned general formulas (2) and (3) are preferable. The groups X, $Ar_1$ to $Ar_3$, and R in general formulas (2) and (3) correspond to X, $Ar_1$ to $Ar_3$, and R in general formula (1) and have the same meaning. The same is true of the preferable groups of X, $Ar_1$ to $Ar_3$, and R. The groups have the same meaning here means that the groups are defined in the same way. In the case where the groups X, $Ar_1$ to $Ar_3$, and R are present in plurality, they may be varied mutually within the range of the aforementioned definition.

The compounds for use in an organic EL device of this invention can be prepared easily by a known method. For example, a compound represented by general formula (2) is prepared by a sequence of reactions shown below with reference to a synthetic example described in Synlett., 2005, No. 1, pp 42-48.

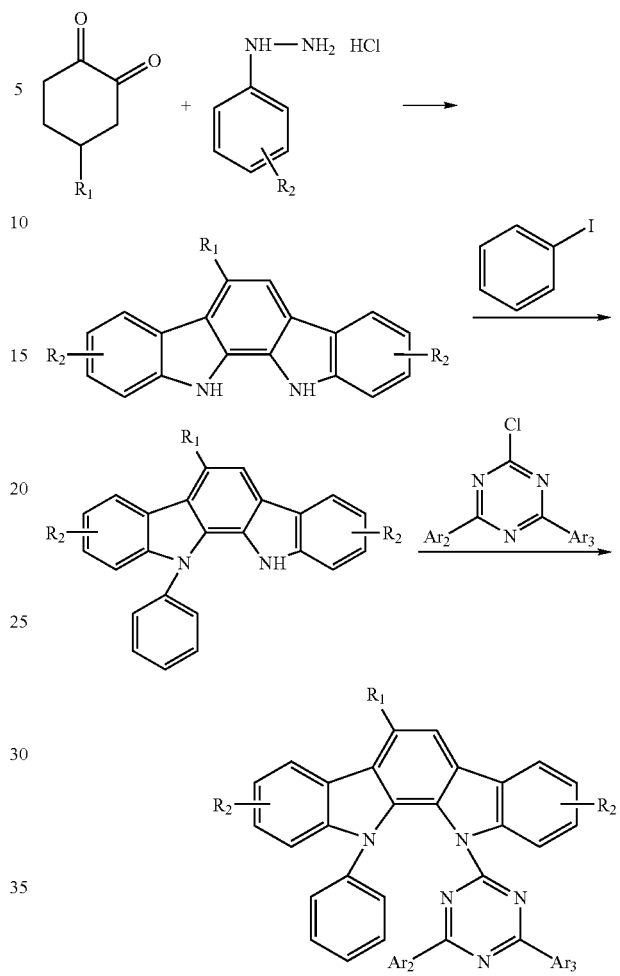

A compound represented by general formula (3) can be prepared by a sequence of reactions shown below with reference to a synthetic example described in Archiv der Pharmazie (Weinheim, Germany), 1987, 320 (3), pp 280-282. In the chemical formulas here, L has the same meaning as $Ar_1$ to $Ar_3$.

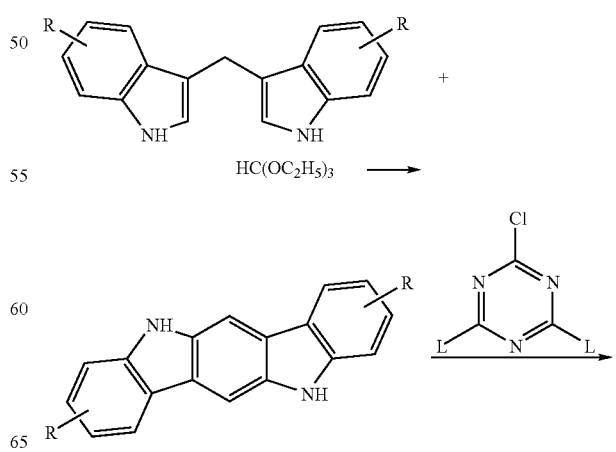

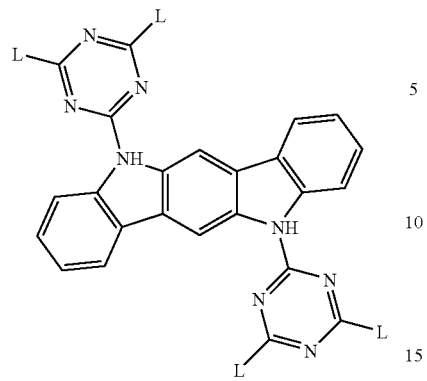
Preferable examples of the compounds represented by general formulas (1), (2), and (3) are shown below, but are not limited thereto.
(1)
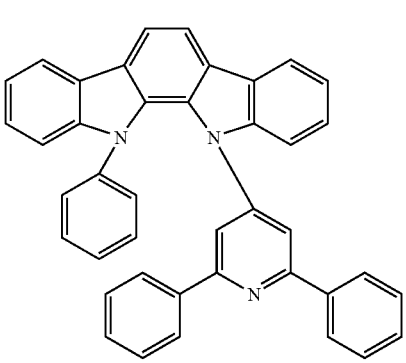
(2)
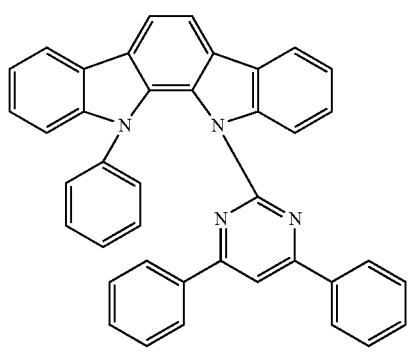
(3)
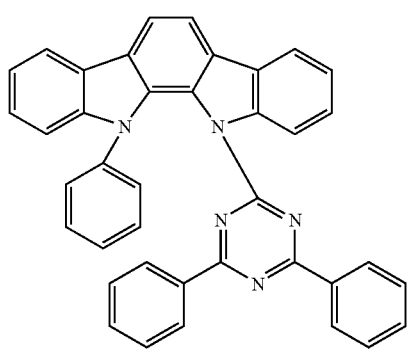
(4)
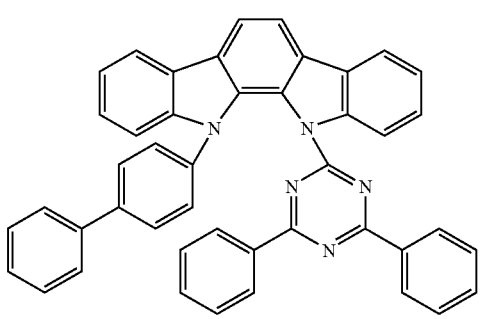
(5)
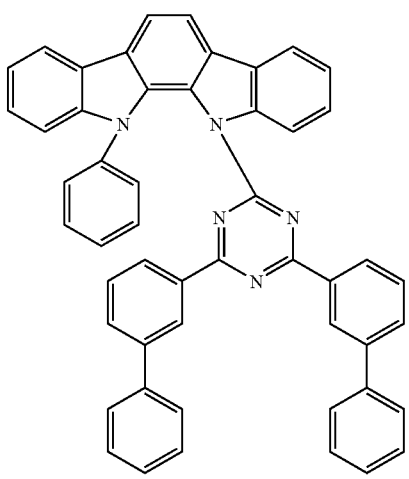
(6)
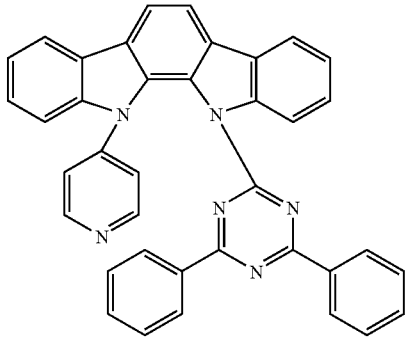
(7)
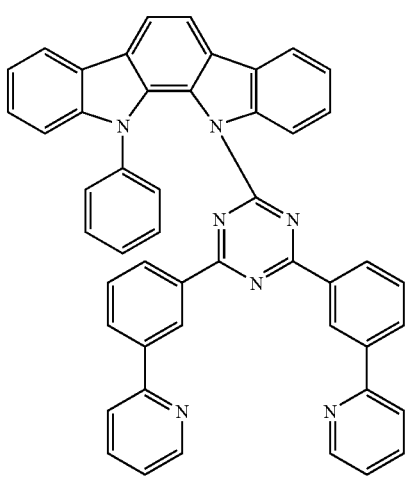

(8)
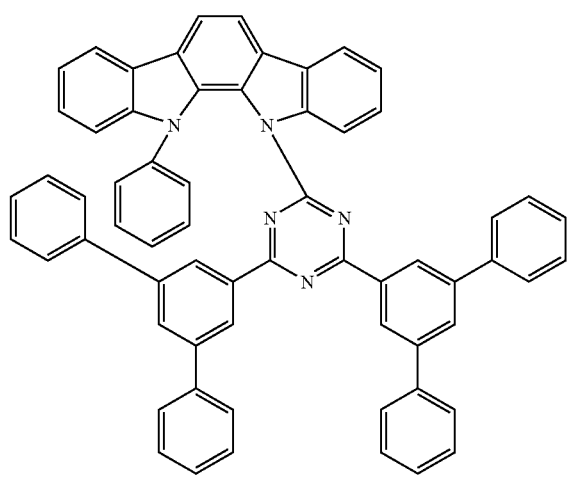
(11)
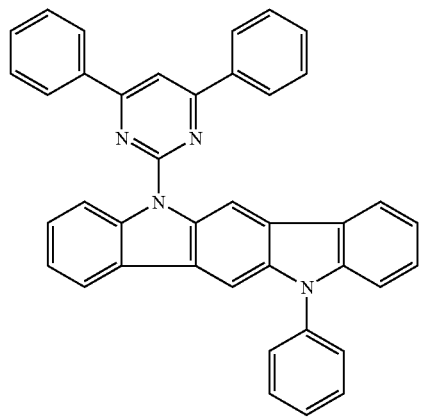
(9)
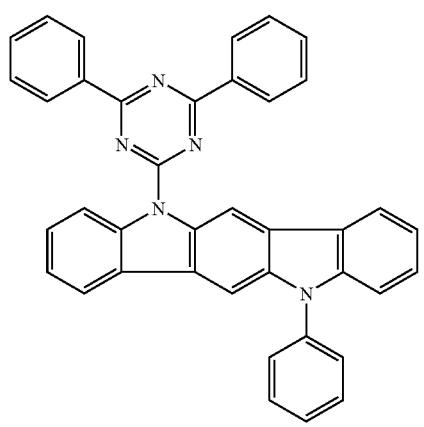
(12)
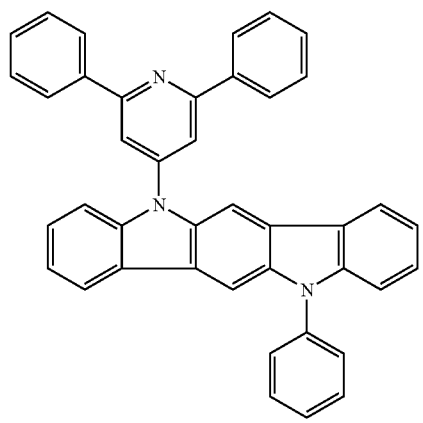
(10)
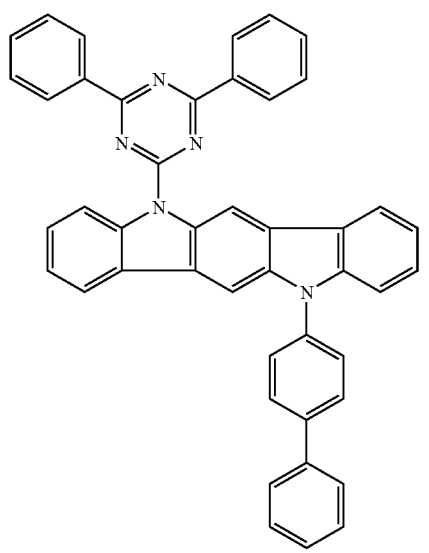
(21)
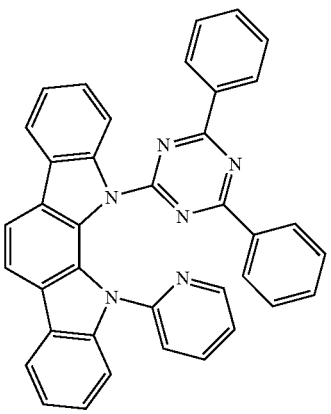

(22)
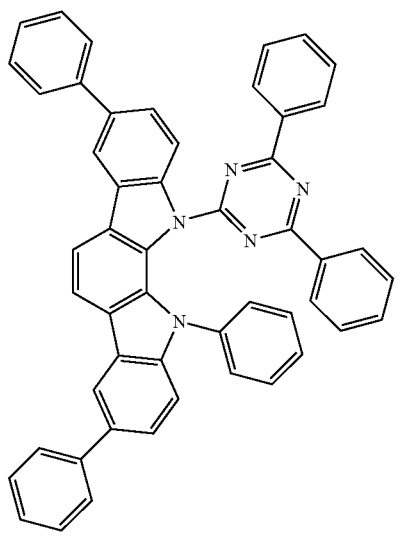
(23)
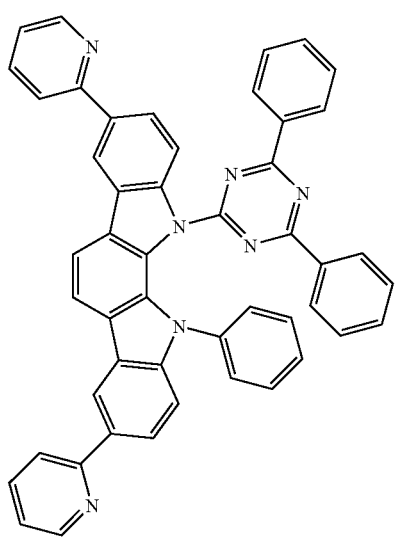
(24)
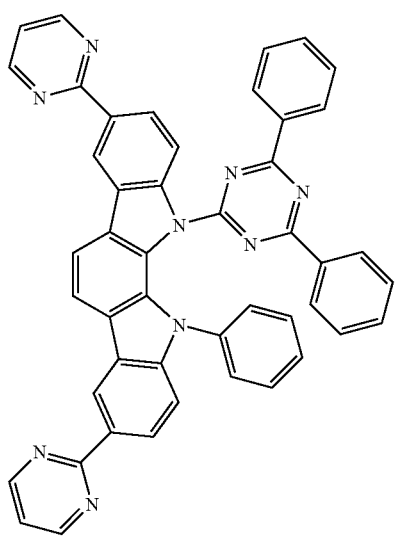
(25)
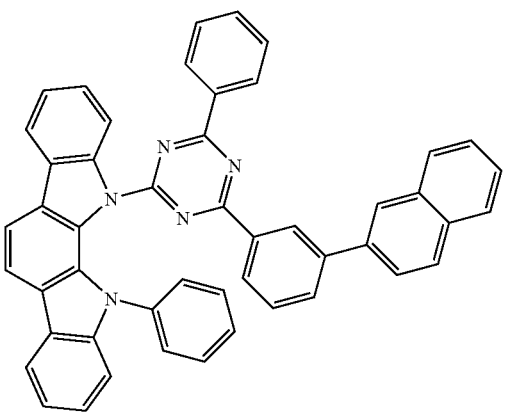
(26)
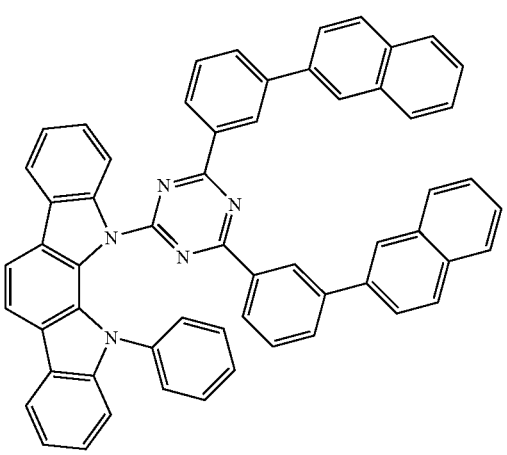
(27)
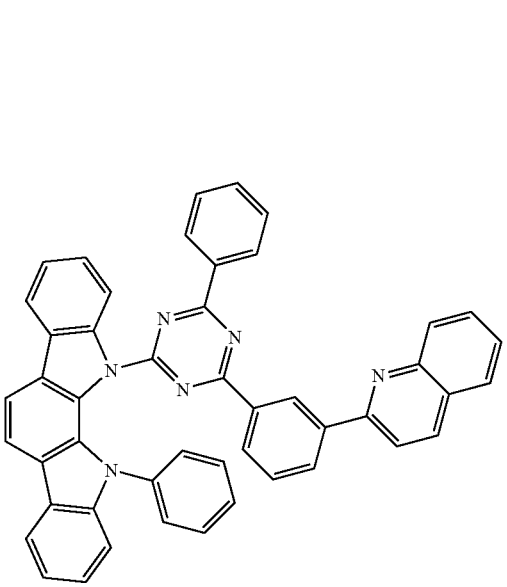

(28)
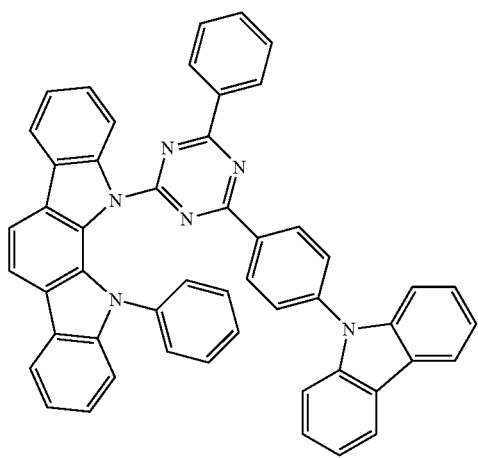
(29)
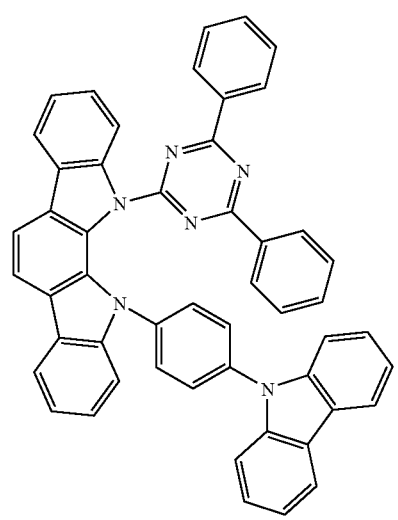
(30)
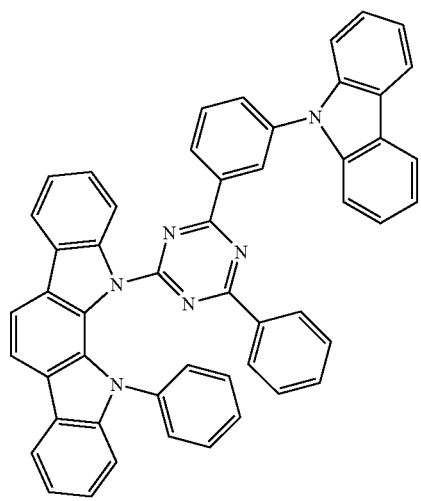
(31)
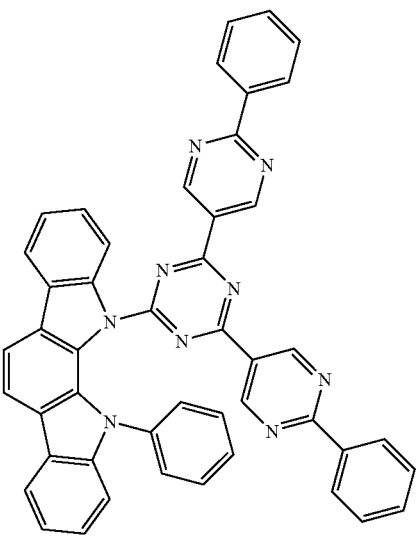
(32)
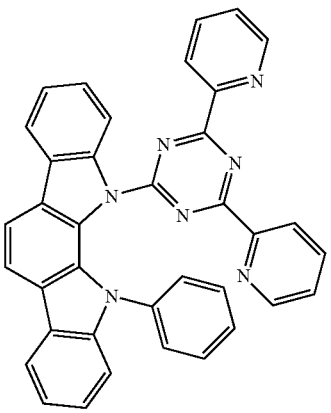
(33)
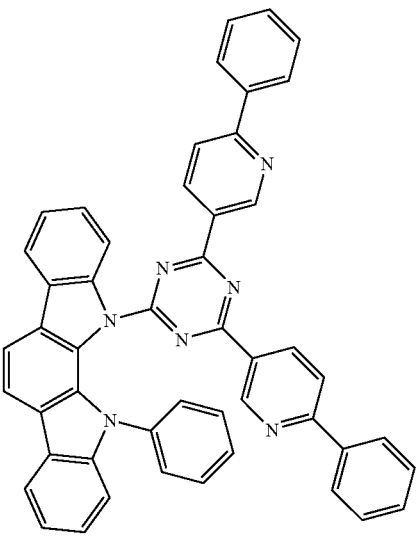

(34)
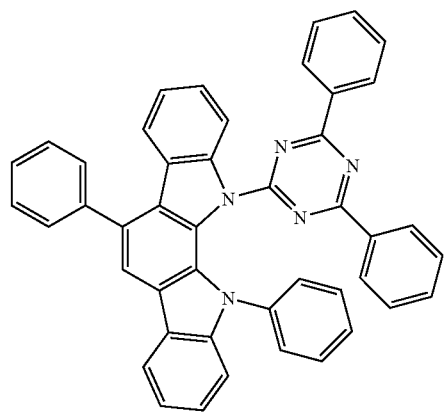
(35)
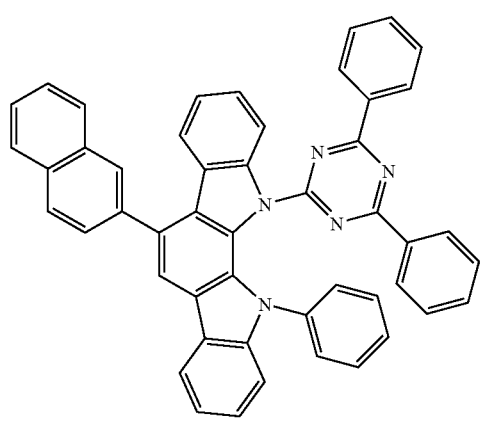
(36)
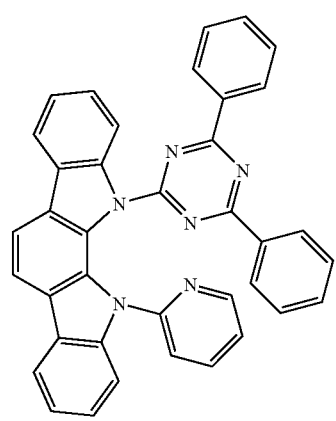
(37)
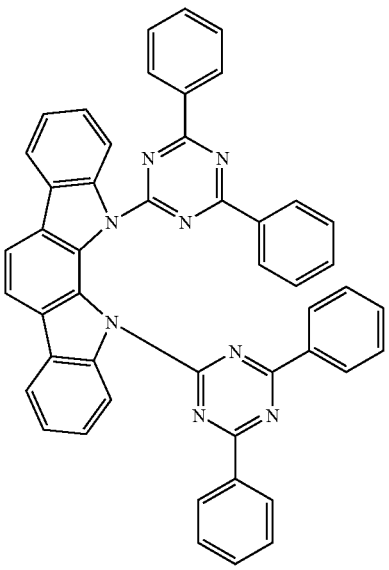
(38)
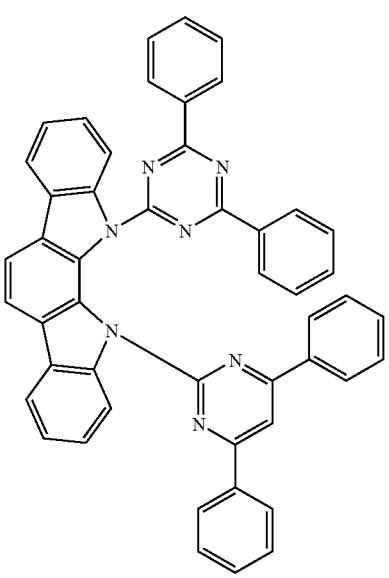
(39)
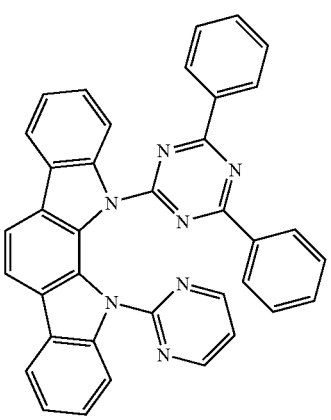

-continued
(40)
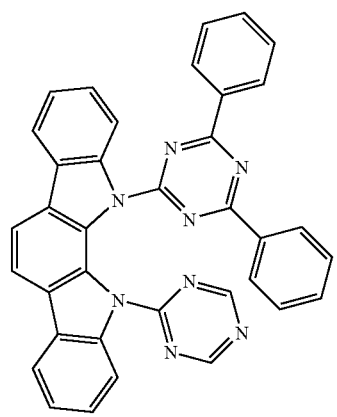
(41)
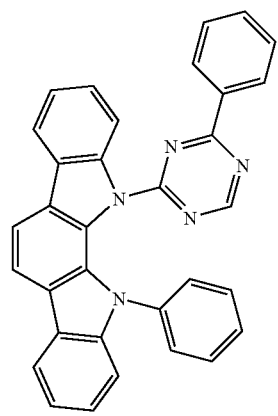
(42)
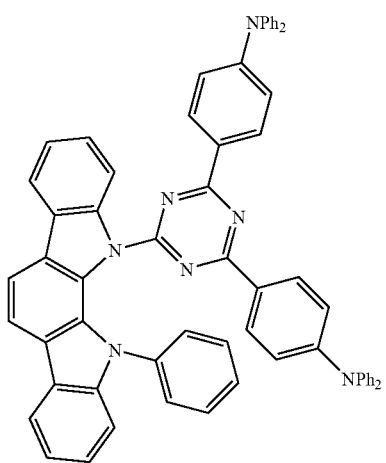
-continued
(43)
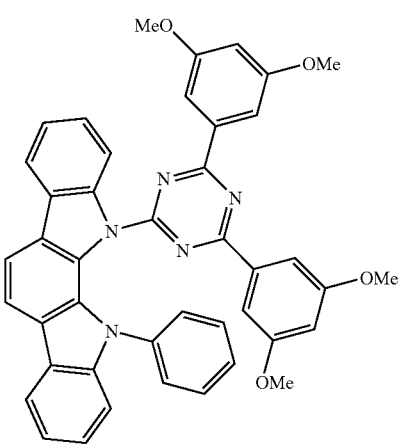
(44)
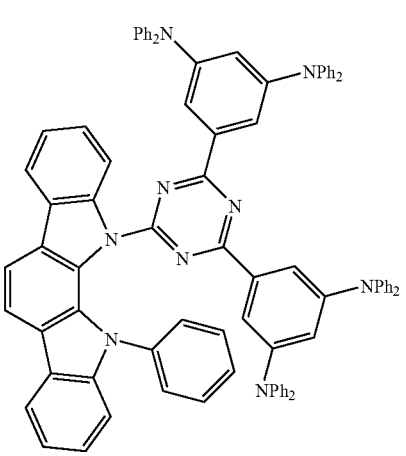
(45)
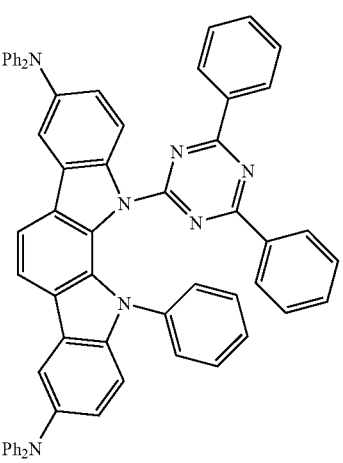

-continued
(46)
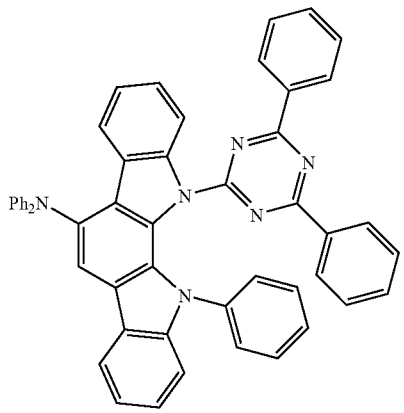
(47)
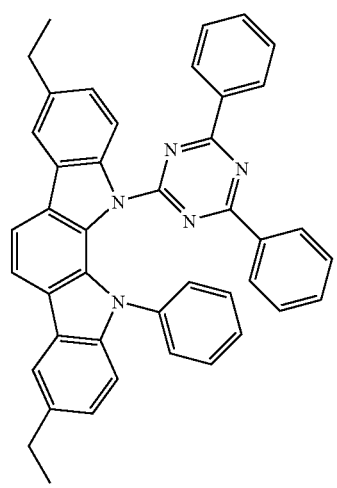
(48)
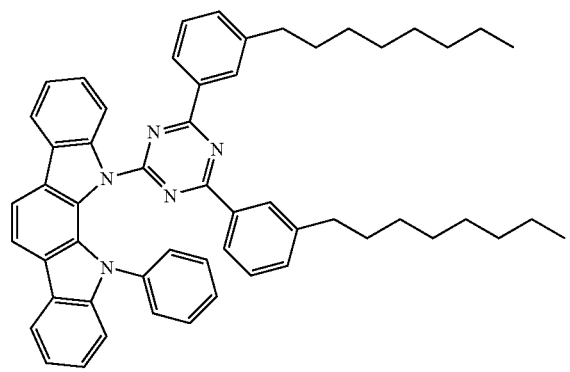
-continued
(49)
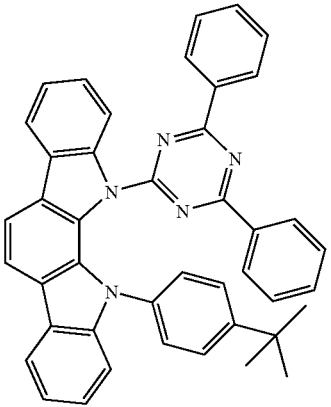
(50)
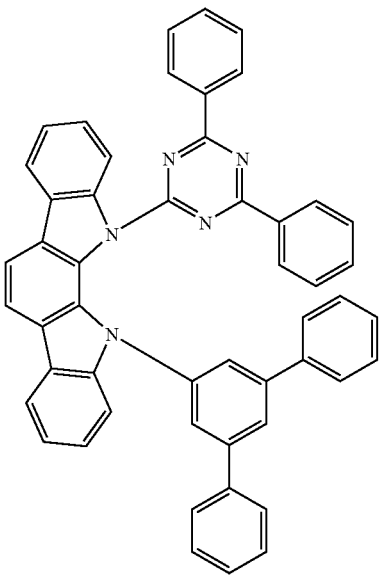
(51)
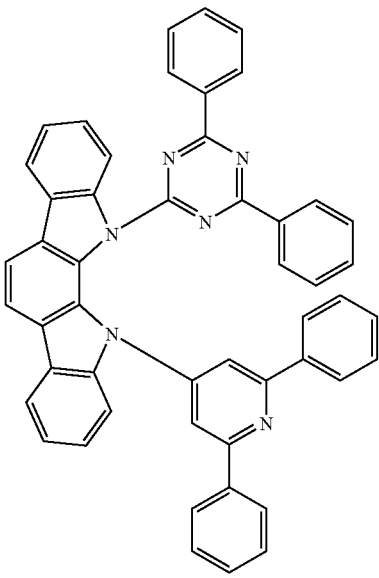

-continued
(52)
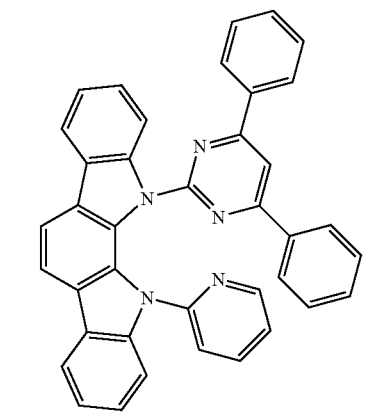
(53)
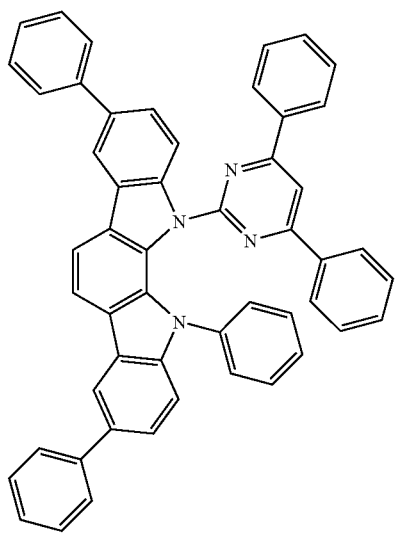
(54)
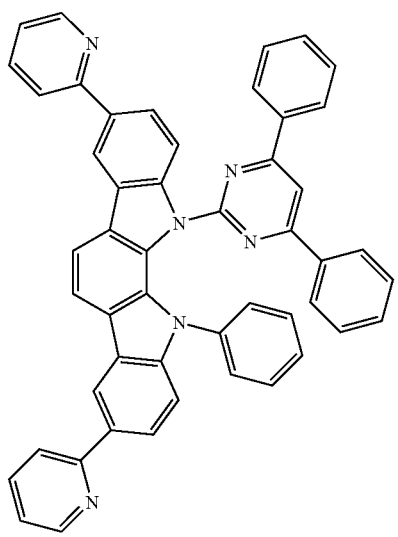
-continued
(55)
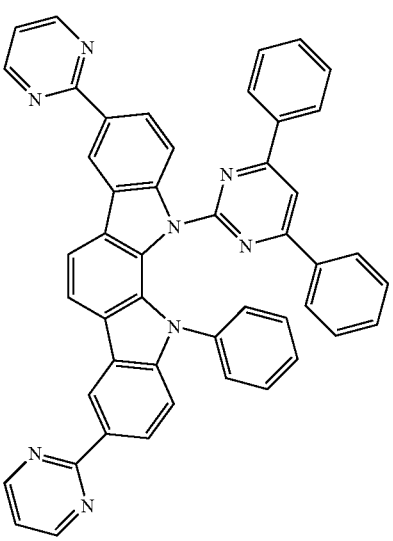
(56)
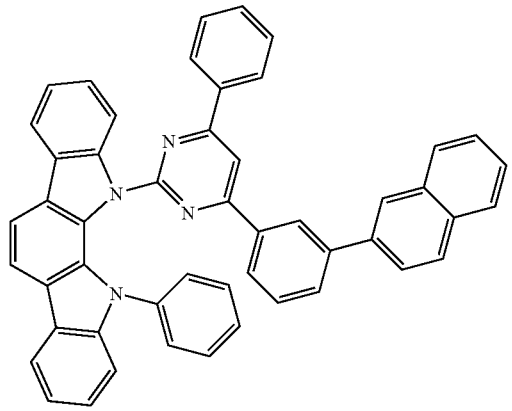
(57)
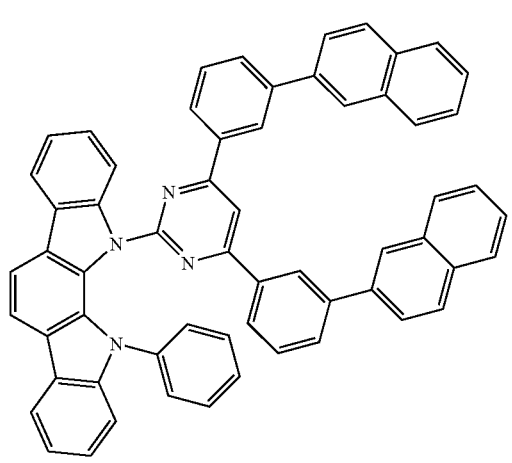

(58)
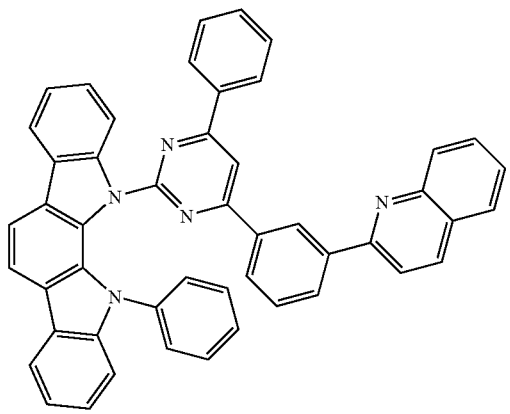
(59)
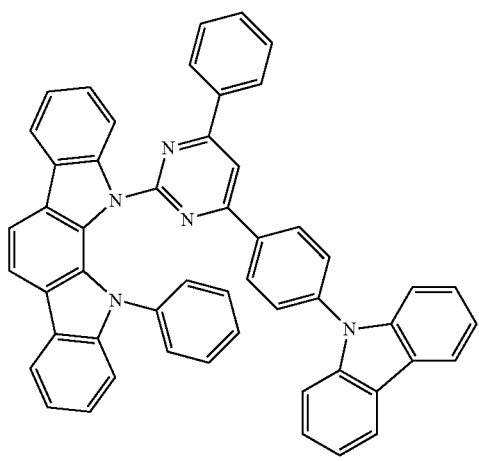
(60)
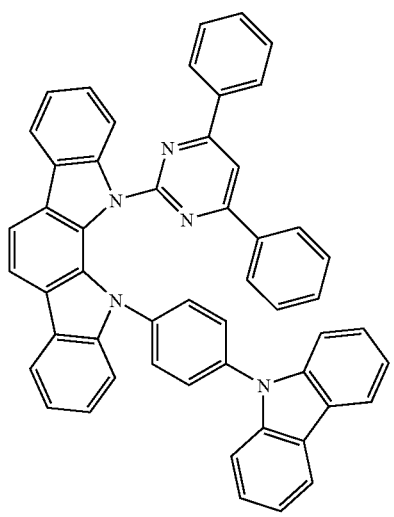
(61)
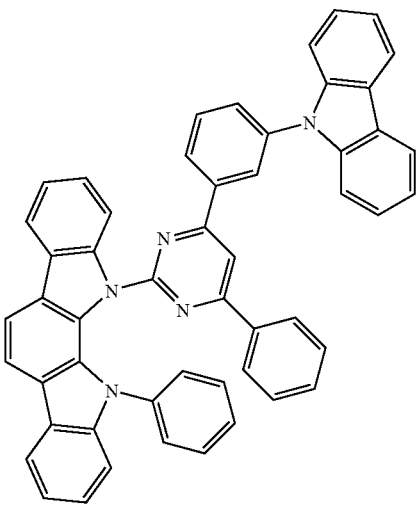
(62)
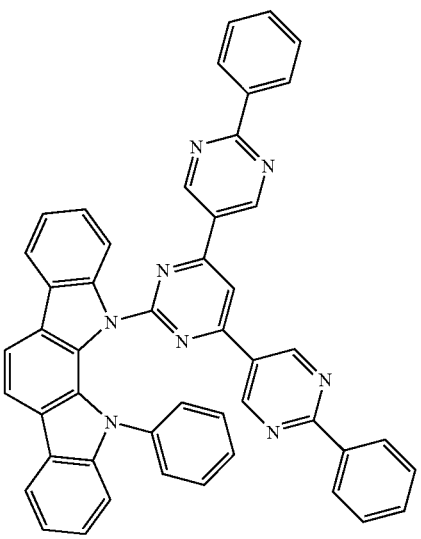
(63)
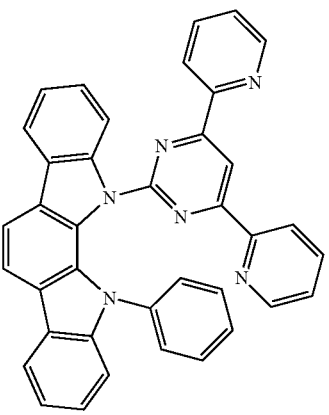

-continued
(64)
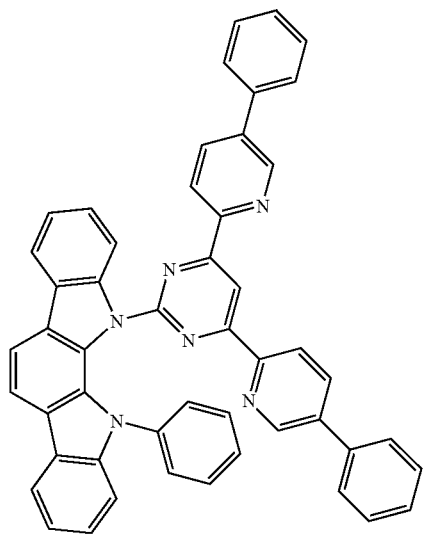
(65)
(66)
(67)
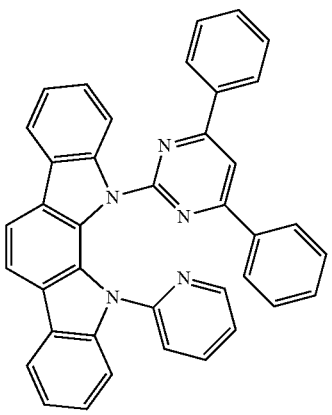
(68)
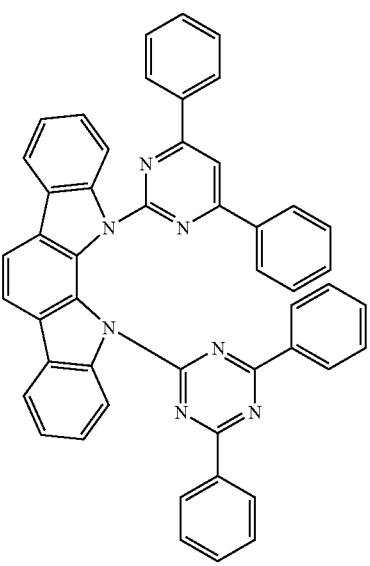
(69)
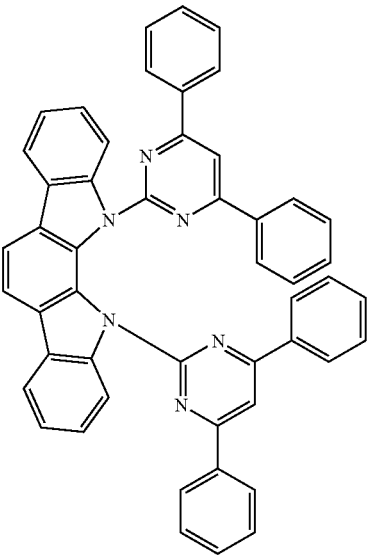

-continued
(70)
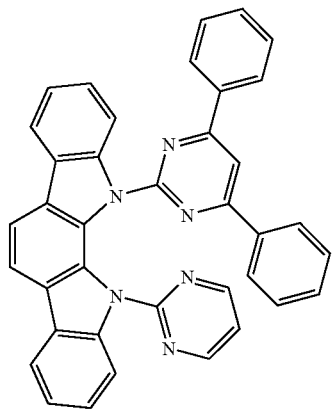
(71)
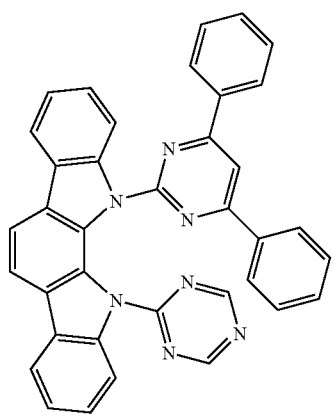
(72)
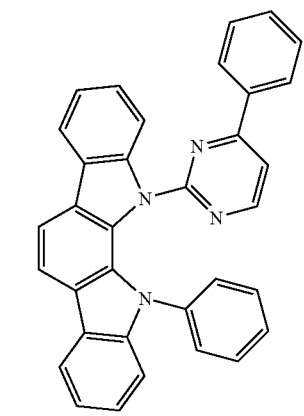
(73)
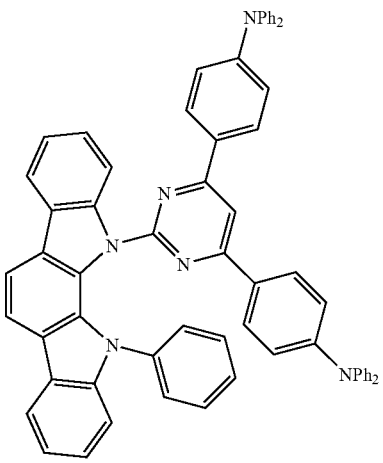
(74)
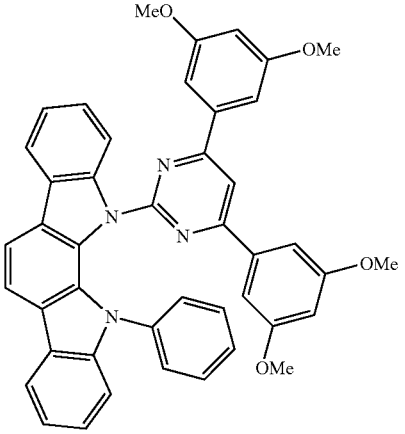
(75)
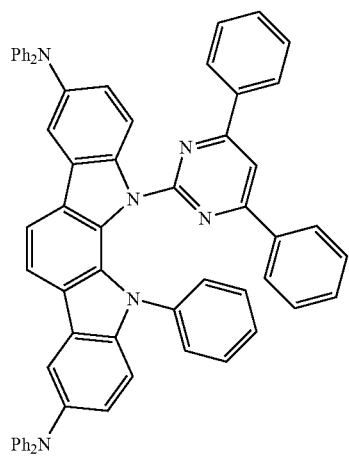

(76)

(77)

(78)

(79)

(80)

(81)

(82)
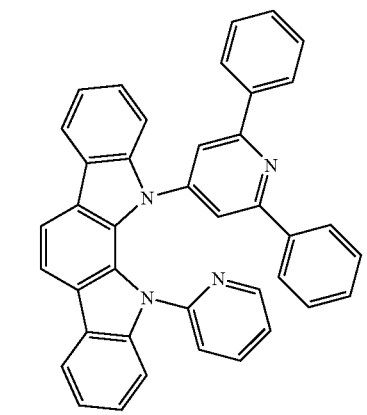
(83)
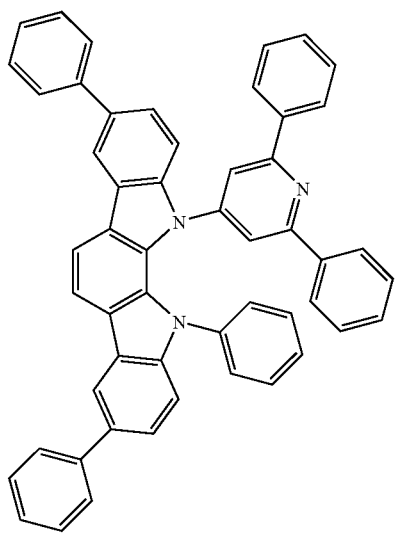
(84)
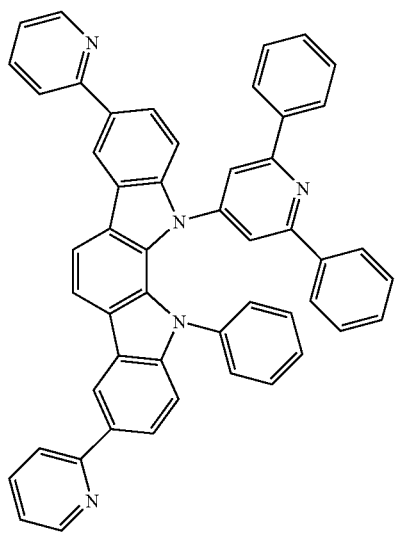
(85)
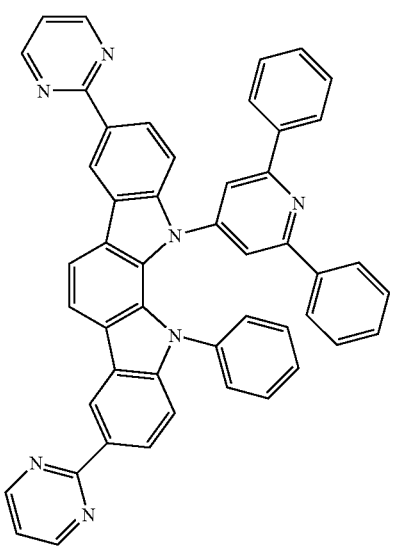
(86)
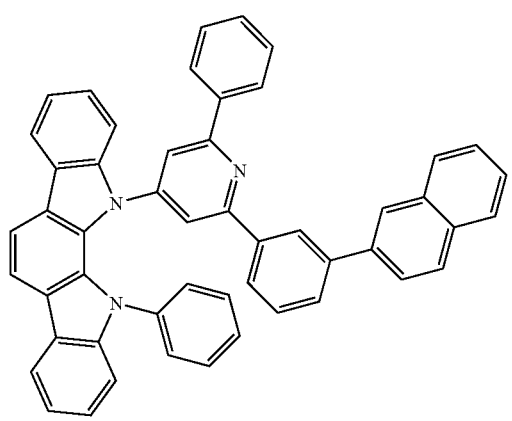
(87)
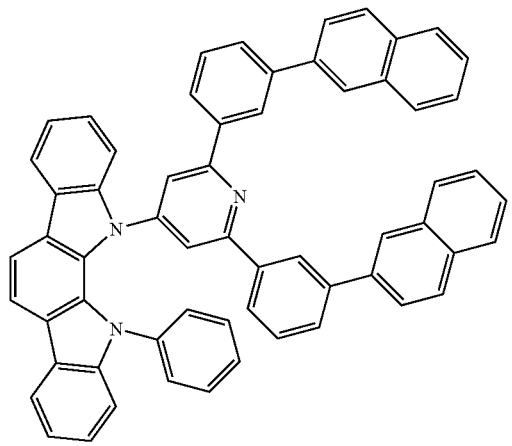

(88)
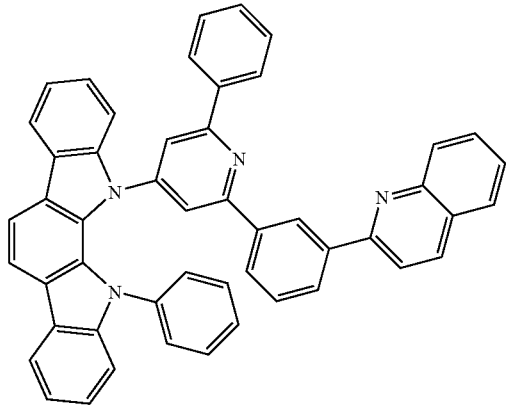
(89)
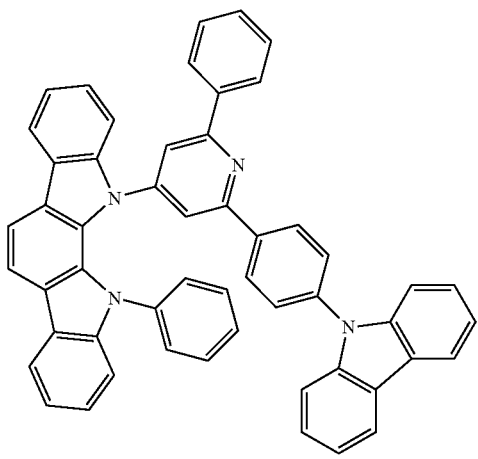
(90)
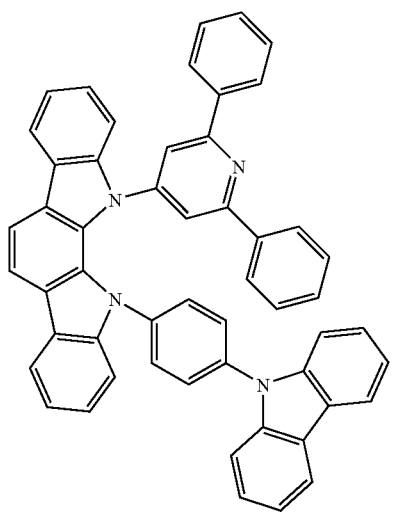
(91)
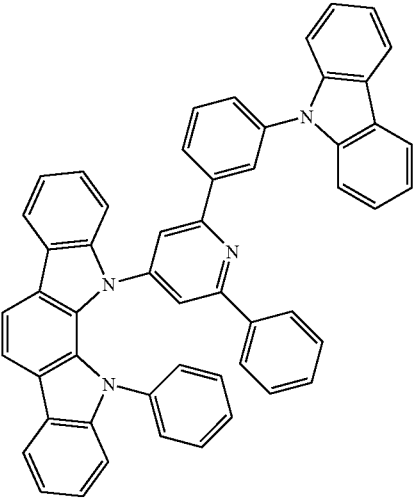
(92)
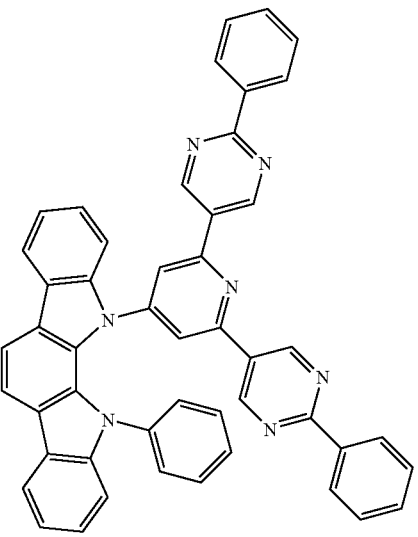
(93)
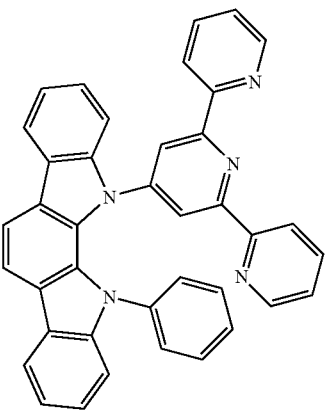

(94)
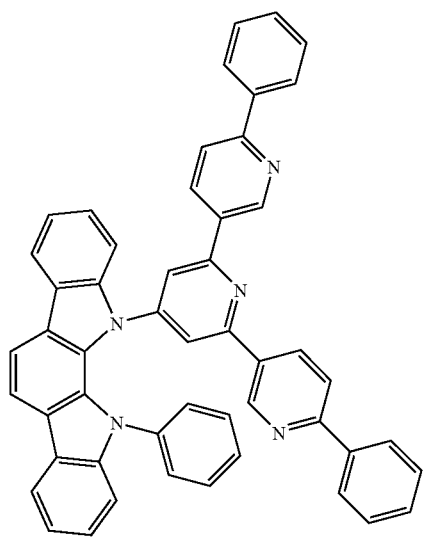
(95)
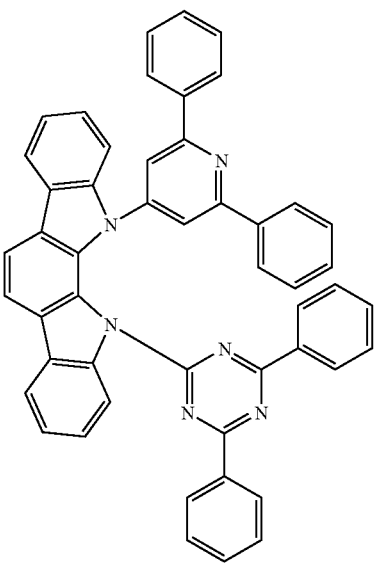
(96)
(97)
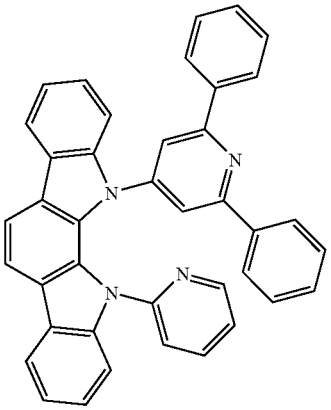
(98)
(99)
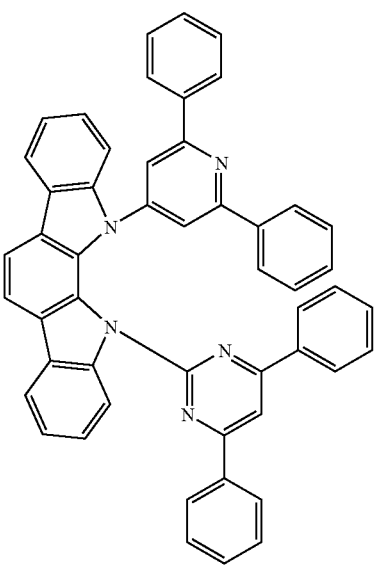

(100)
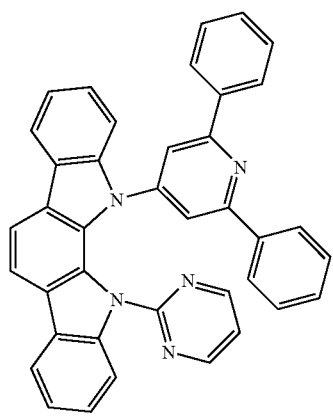
(101)
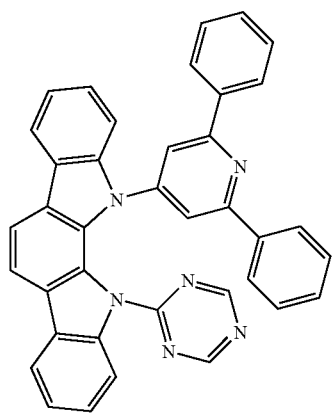
(102)
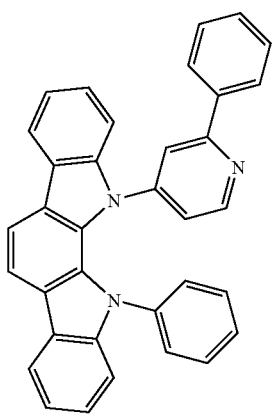
(103)
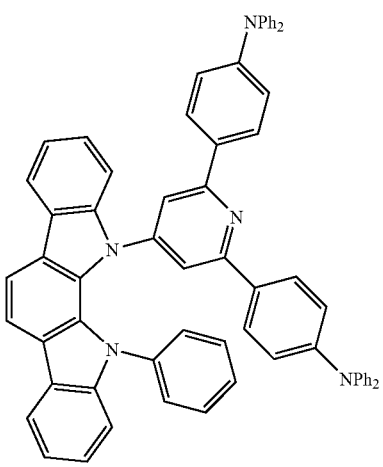
(104)
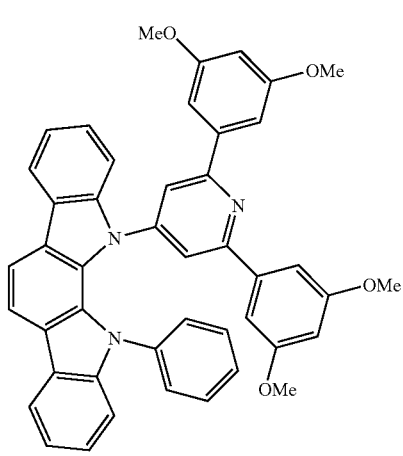
(105)
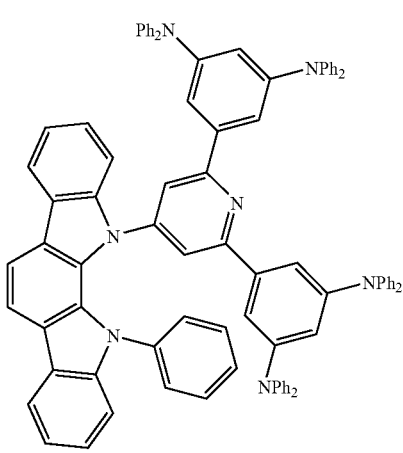

-continued
(106)
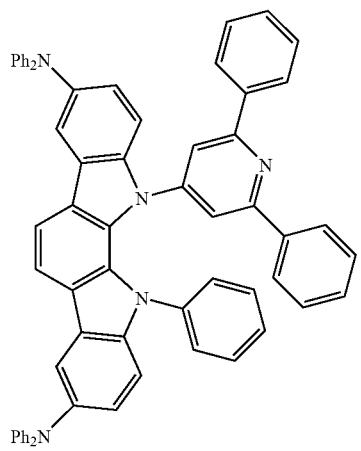
(107)
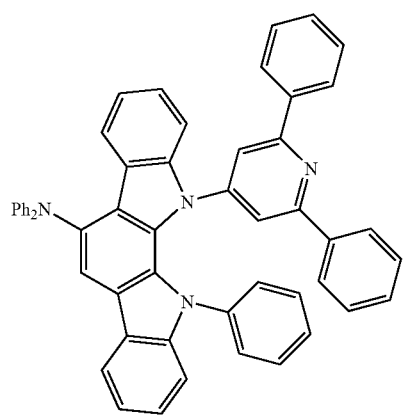
(108)
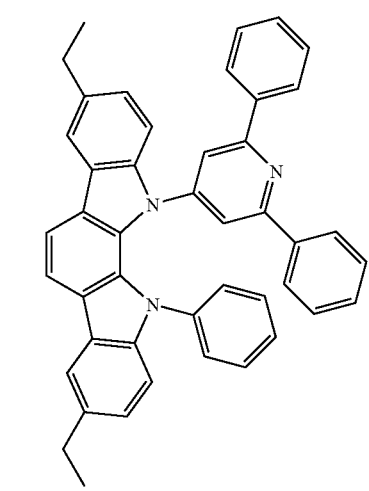
(109)
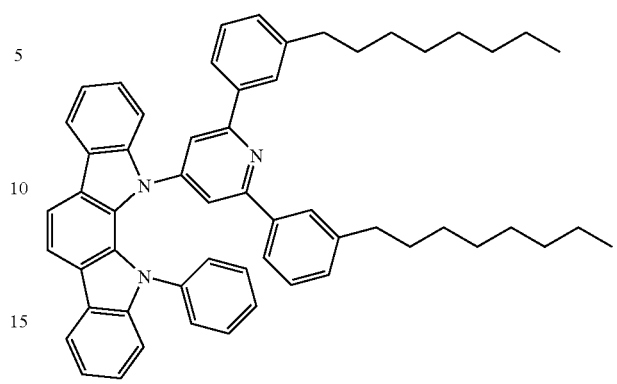
(110)
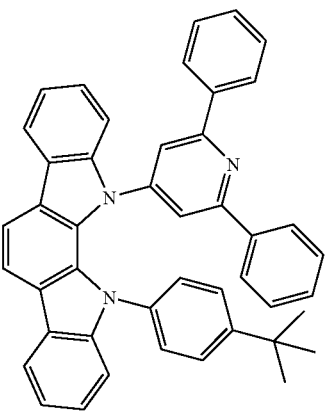
(111)
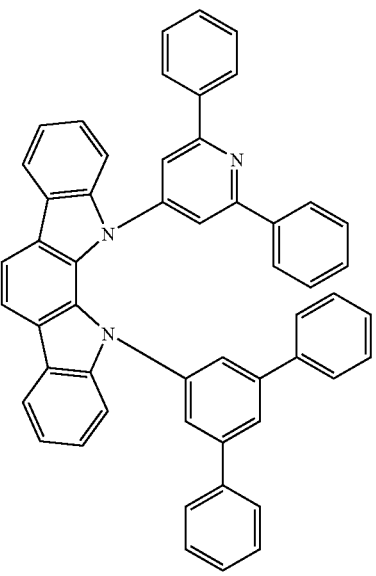

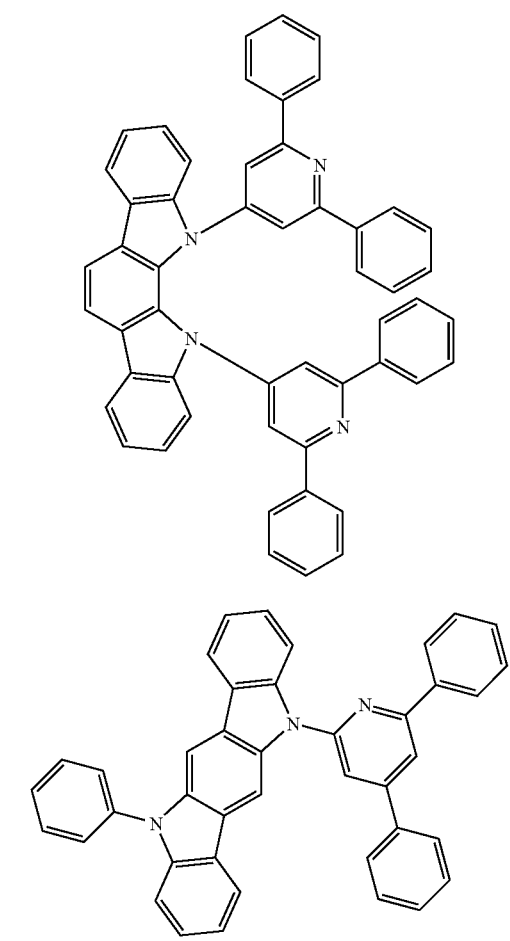
(112)
(113)
(114)
(115)
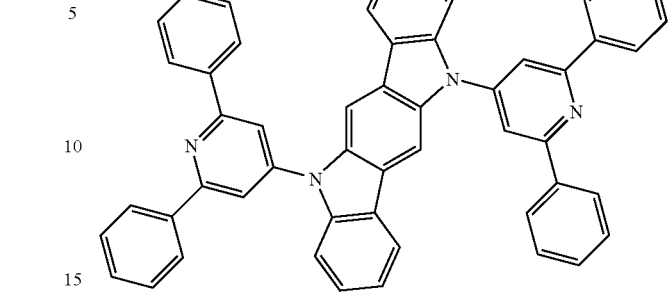
(116)
(117)
(118)
(119)

(120)
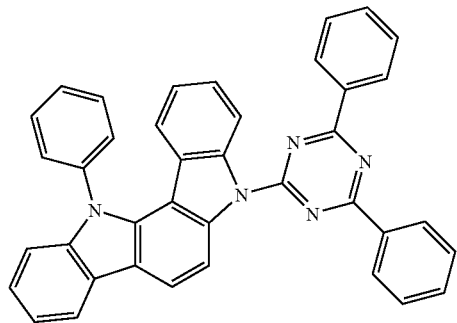
(121)
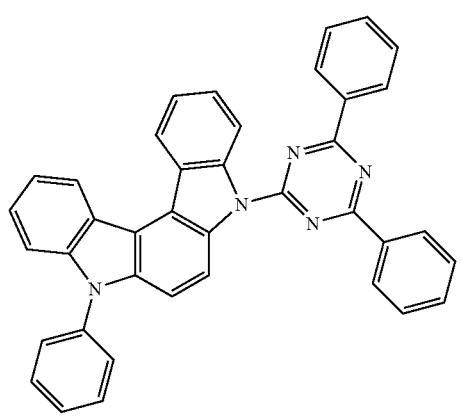
(122)
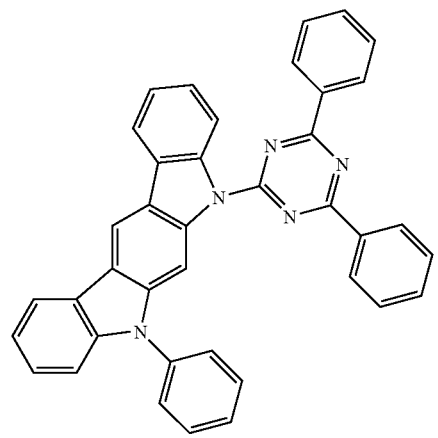
(123)
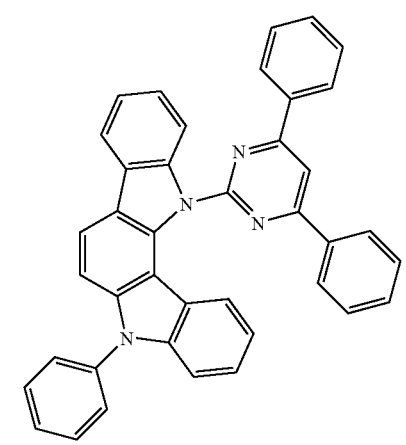
(124)
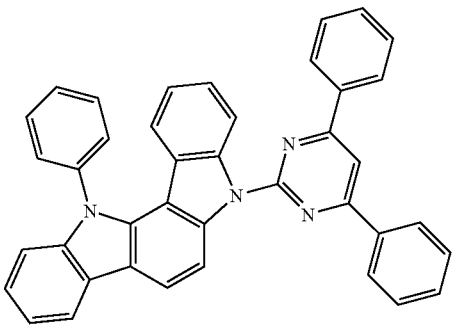
(125)
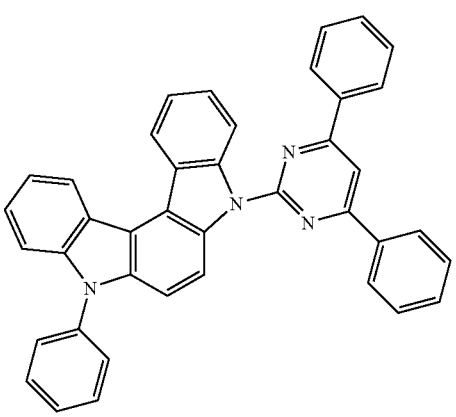
(126)
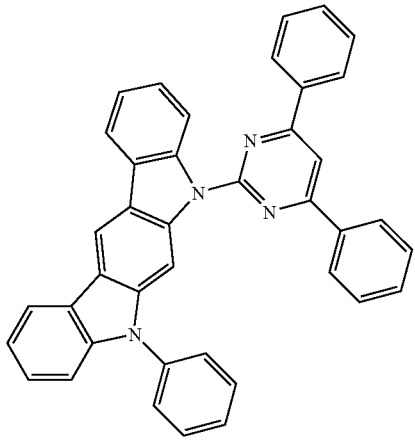
(127)
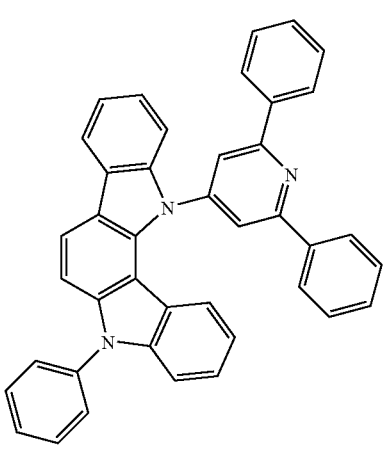

(128) 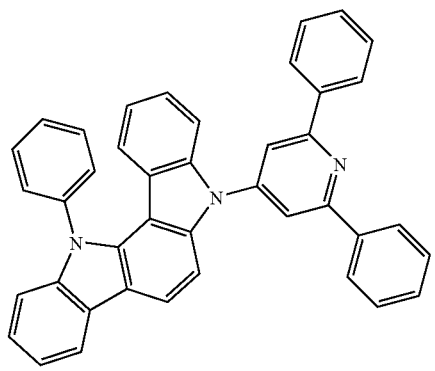

(129) 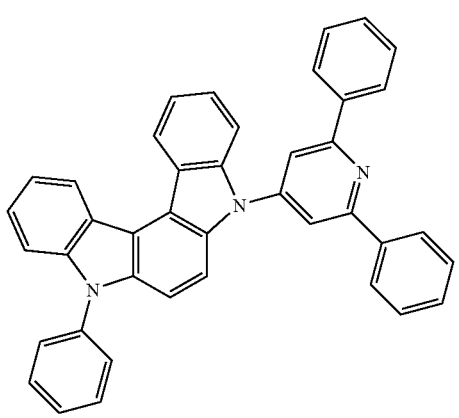

(130) 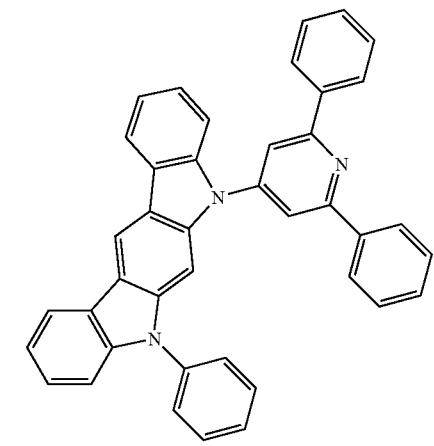

(131) 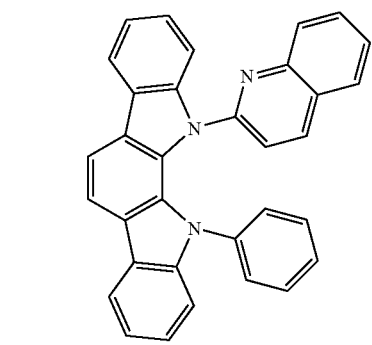

(132) 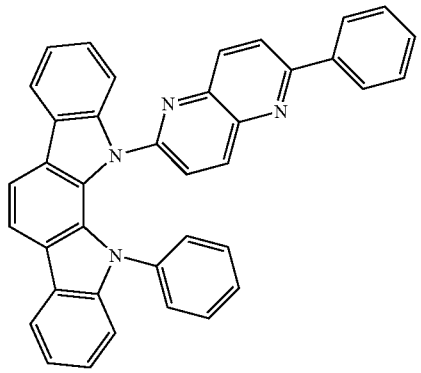

An excellent organic electroluminescent device is provided by incorporating the compound of this invention in its organic layer. Preferably, the said compound is incorporated in at least one organic layer selected from a light-emitting layer, a hole-transporting layer, an electron-transporting layer, and a hole-blocking layer. More preferably, the said compound is incorporated as a host material in a light-emitting layer containing a phosphorescent dopant.

An organic electroluminescent device to be provided by this invention advantageously contains a light-emitting layer disposed between an anode and a cathode stacked one upon another on a substrate and the said light-emitting layer contains a phosphorescent dopant and the aforementioned compound for use in an organic EL device as a host material. An organic EL device constituted of a substrate, an anode, a cathode, and a light-emitting layer manages to function; however, it is preferable that a hole-injecting/transporting layer is disposed between the anode and the light-emitting layer and an electron-injecting/transporting layer is disposed between the cathode and the light-emitting layer and, further, a hole-blocking layer is disposed between the light-emitting layer and the electron-injecting/transporting layer.

Phosphorescent dopants to be used in the light-emitting layer are preferably organic metal complexes containing at least one metal selected from ruthenium, rhodium, palladium, silver, rhenium, osmium, iridium, platinum, and gold. Such organic metal complexes are known in the aforementioned patent documents and elsewhere and a suitable material can be chosen from them and used in this invention.

Preferable phosphorescent dopants include complexes having a noble metal element such as Ir in the center, typically Ir(ppy)3, complexes such as Ir(bt)2·acac3, and complexes such as PtOEt$_3$. Examples of these complexes are shown below, but are not limited thereto.

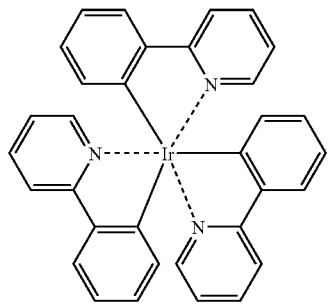

47
-continued
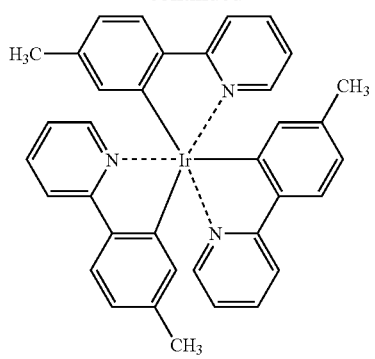
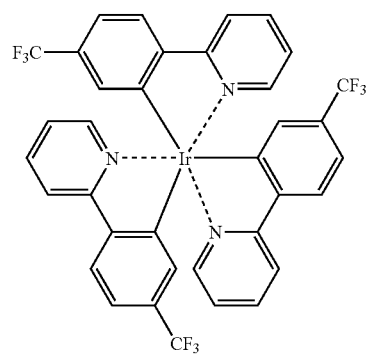
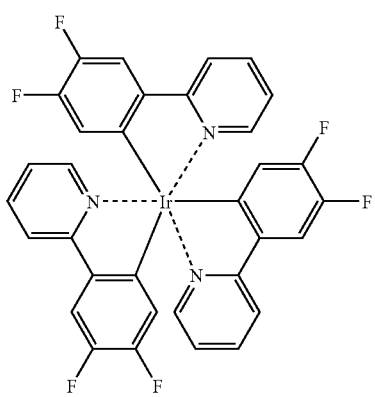
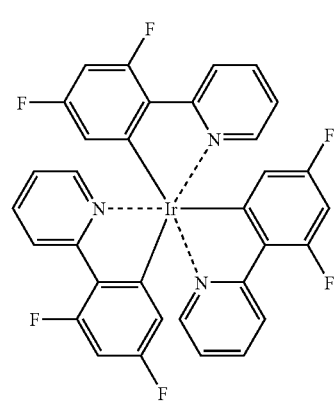
48
-continued
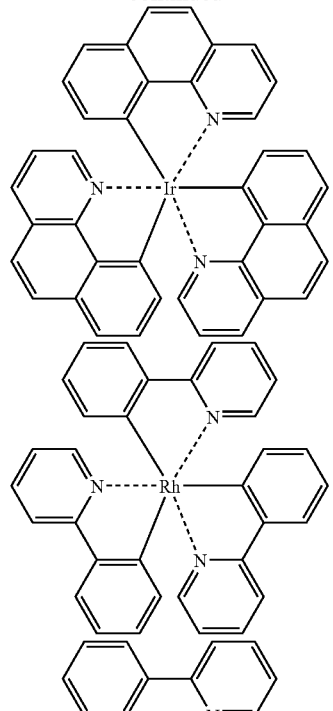
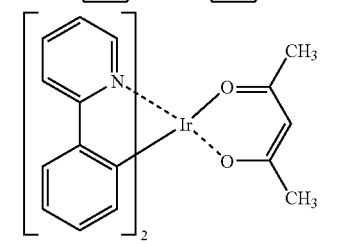
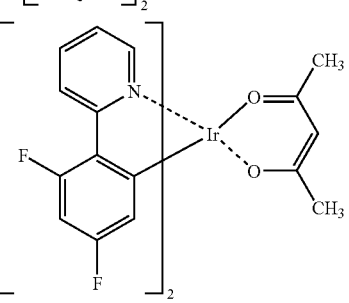
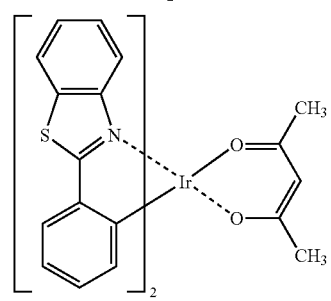

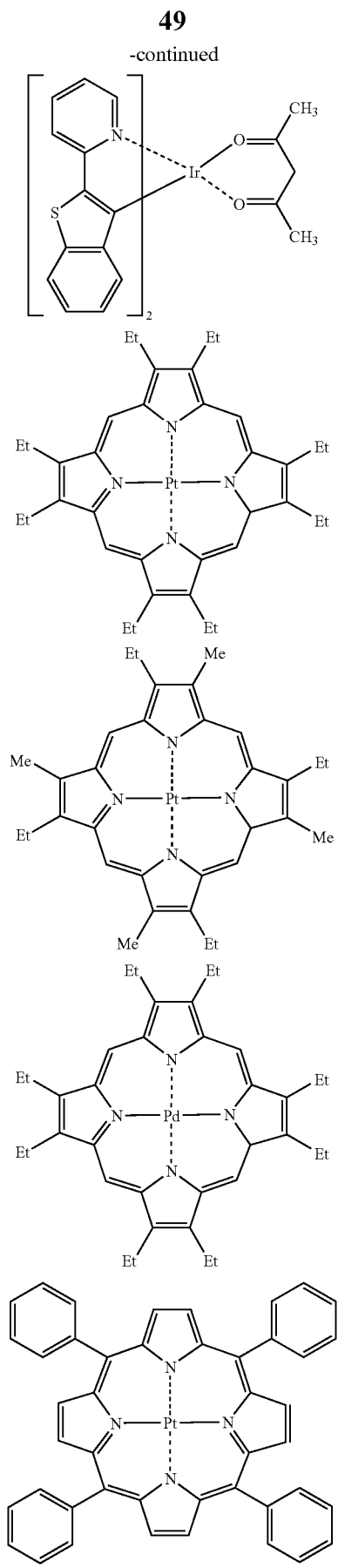
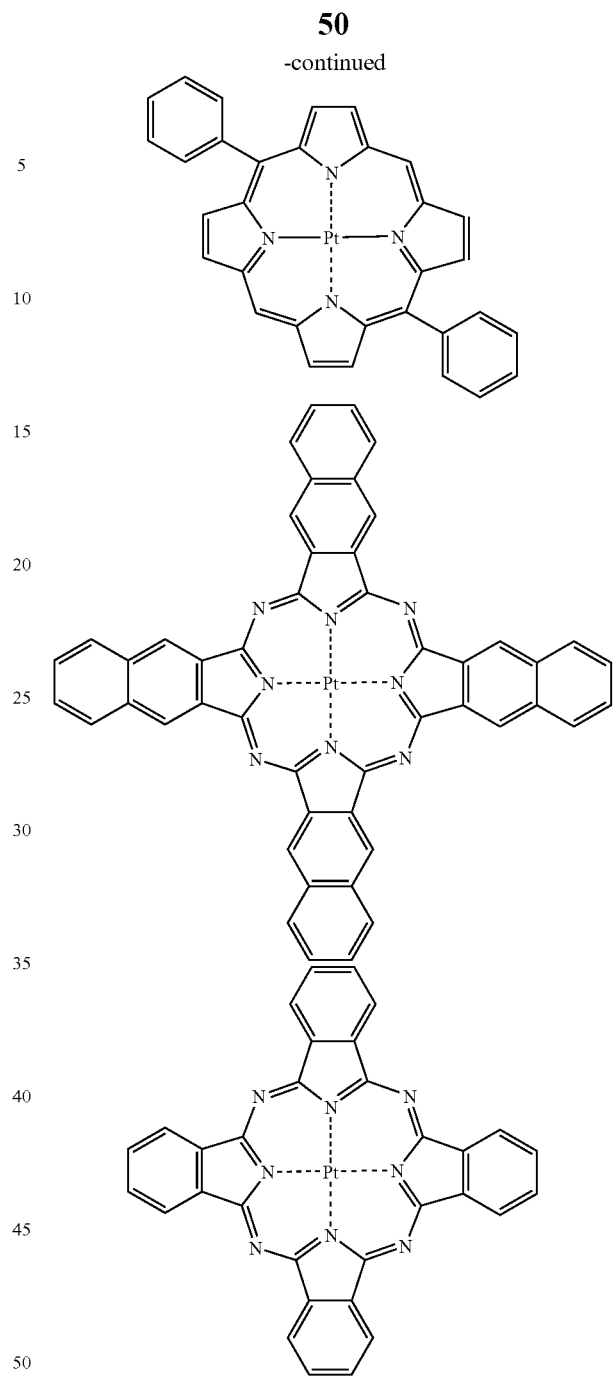

The content of the aforementioned phosphorescent dopant in the light-emitting layer is preferably in the range of 5 to 10 wt %.

The structure of an organic EL device to be provided by this invention will be explained with reference to the drawing, but is not limited thereto.

FIG. 1 schematically shows the structure of an example of organic EL device generally used in this invention and the numbers in FIG. 1 respectively designate the following; 1 substrate, 2 anode, 3 hole-injecting layer, 4 hole-transporting layer, 5 light-emitting layer, 6 electron-transporting layer, and 7 cathode. The organic EL device of this invention comprises a substrate, an anode, a light-emitting layer, and a cathode as essential layers; in addition to the essential layers, the device preferably has a hole-injecting/transporting layer and an electron-injecting/transporting layer and, further, has a hole-blocking layer disposed between the light-emitting layer and the electron-injecting/transporting layer. The term hole-injecting/transporting layer means a hole-injecting layer and/or a hole-transporting layer and the term electron-injecting/transporting layer means an electron-injecting layer and/or an electron-transporting layer.

It is possible to construct a device with a structure that is the reverse of the one shown in FIG. 1 by stacking the cathode 7, the electron-transporting layer 6, the light-emitting layer 5, the hole-transporting layer 4, and the anode 2 one upon another in this order on the substrate 1 and, as described earlier, it is possible to dispose the organic EL device of this invention between two substrates at least one of which is highly transparent. In this case of the reverse structure, a layer or layers may be added or omitted if necessary.

The organic EL device of this invention is applicable to a single device, a device with its structure arranged in array, or a device in which the anode and the cathode are arranged in X-Y matrix. The organic EL device of this invention produces remarkable improvements in luminous efficiency and driving stability over the conventional devices utilizing emission of light from the excited singlet state by incorporating a compound of specific skeleton and a phosphorescent dopant in its light-emitting layer and it can perform excellently when applied to full-color or multicolor panels.

EXAMPLES

This invention will be described in more detail below with reference to the examples; however, it will not be limited to these examples and it can be reduced to practice in various modes unless such practice exceeds the substance of the invention. The compound numbers used in the examples correspond to the numbers assigned to the indolocarbazole derivatives listed earlier together with their chemical formulas.

Example 1

In a 2000-ml three-necked flask that had been deaerated and filled with nitrogen were placed 33.3 g (297.0 mmoles) of 1,2-cyclohexanedione and 86.0 g (594.7 mmoles) of phenylhydrazine hydrochloride, then 1000 ml of ethanol was added, and the mixture was stirred. To the flask was added dropwise 3.0 g (30.6 mmoles) of concentrated sulfuric acid over 5 minutes. The mixture was then heated to 65° C. and stirred at this temperature for 4 hours. The mixture was cooled to room temperature and the violet brown crystals formed were collected by filtration, reslurried twice with 500 ml of ethanol, and dried under reduced pressure to give 80.0 g (280.5 mmoles, 96.3% yield) of a violet brown powder.

Then, 72.0 g (261.5 mmoles) of the violet brown powder obtained above was placed in a 1000-ml three-necked flask, 720 g of acetic acid and 72.0 g of trifluoroacetic acid were added, and the mixture was stirred. The mixture was then heated to 100° C. and stirred at this temperature for 15 hours. The mixture was cooled to room temperature, the yellow crystals formed were collected by filtration, rinsed with 200 ml of acetic acid, then rinsed with 200 ml of hexane, and dried under reduced pressure to give 30.0 g (117.1 millimoles, 44.8% yield) of white powder A' or indolo[2,3-a]carbazole.

In a 1000-ml three-necked flask that had been deaerated and filled with nitrogen were placed 26.0 g (101.4 mmoles) of the white powder obtained above, 122.7 g (601.4 mmoles) of iodobenzene, 54.7 g (287.2 mmoles) of copper iodide, and 66.7 g (482.6 mmoles) of potassium carbonate, then 800 ml of quinoline was added, and the mixture was stirred. The mixture was then heated to 190° C. and stirred at this temperature for 72 hours. The mixture was cooled to room temperature, 500 ml of water and 500 ml of dichloromethane were added, the mixture was stirred, and the yellow crystals formed were filtered. The filtrate was transferred to a 2000-ml separatory funnel and separated into an organic layer and an aqueous layer. The organic layer was washed three times with 500 ml of water and dried over magnesium sulfate, the magnesium sulfate was filtered off, and the solvent was distilled off under reduced pressure. The residue was purified by column chromatography to give 13.7 g (41.2 mmoles, 40.6% yield) of white solid A or 11-phenylindolo[2,3-a]carbazole.

Then, 12.5 g (0.068 mole) of cyanuric chloride and 55 ml of dehydrated THF were placed in a 200-ml three-necked flask that had been deaerated and filled with nitrogen and the mixture was stirred in an ice bath in a stream of nitrogen. Then, to the flask was added dropwise 105.6 g (0.186 mole) of a 32% THF solution of phenylmagnesium bromide over 2 hours while keeping the temperature at 15° C. or below during the addition. Upon completion of the dropwise addition, the mixture was stirred continuously for 1.5 hours. Thereafter, 80 g of toluene was added to the flask, the mixture was cooled in an ice bath, and 76.5 g (0.254 mole) of a 12% aqueous solution of HCl was added dropwise to the flask over 15 minutes while keeping the temperature at 30° C. or below during the addition. The contents of the flask were transferred to a 500-ml separatory funnel and separated into an organic layer and an aqueous layer. The organic layer was washed three times with 100 ml of water and dried over magnesium sulfate, the magnesium sulfate was filtered off, the solvent was distilled off under reduced pressure, and 21.1 g of a crude product was obtained. Then, 110 g of methanol was added to the crude product, the mixture was stirred for 1 hour, the precipitate was filtered off, and the filtrate was dried in a vacuum dryer to give 14.5 g (6.5 mmoles, 50.2% yield) of white solid B or 2-chloro-4,6-diphenyl-1,3,5-triazine.

Then, 2.18 g (50.0 mmoles) of a 55% dispersion of sodium and 70 ml of dehydrated N,N'-dimethylformamide were placed in a 2000-ml three-necked flask that had been deaerated and filled with nitrogen and the mixture was stirred in a stream of nitrogen. A solution of 13.5 g (40.6 mmoles) of white solid A obtained above in 150 ml of dehydrated N,N'-dimethylformamide was prepared and added dropwise to the flask over 10 minutes. Upon completion of the dropwise addition, the mixture was stirred continuously for 1 hour. Thereafter, 10.4 g (39.0 mmoles) of white solid B obtained above was dissolved in 150 ml of dehydrated N,N'-dimethylformamide and the resulting solution was added dropwise to the flask over 1 hour. Upon completion of the dropwise addition, the mixture was stirred continuously for 3 hours. Then, 600 g of water was added and the crystals separated were collected by filtration, reslurried twice with 300 g of water, then reslurried with 300 g of methanol, and dried in a vacuum dryer to give 21.0 g of yellow crystals.

Then, 21.0 g of the yellow crystals was dissolved in 108.6 g of THF in a 1000-ml flask and 660 g of methanol was added dropwise to the flask. The precipitate was filtered off and the filtrate was dried in a vacuum dryer to give 12.7 g (22.6 mmoles, 54.6% yield) of a yellow solid or Compound 3.

Compound 3 gave a molecular ion with a mass of 563 by EI-MS (M+1) and its melting point was 263° C.

Example 2

Compound 3 was deposited on a glass substrate from an evaporation source at a rate of 0.1 nm/sec to a thickness of 50 nm by the vacuum deposition process at a degree of vacuum of 4.0×10⁻⁴ Pa. The thin film thus formed was evaluated by a fluorometer and emission of light was observed.

Separately, Compound 3 and Ir(ppy)3 were co-deposited on a glass substrate from different evaporation sources at a rate of 0.1 nm/sec to a thickness of 50 nm by the vacuum deposition process at a degree of vacuum of 4.0×10⁻⁴ Pa while controlling the concentration of Ir(ppy)3 at 7.0%. The thin film thus formed was evaluated by a fluorometer. The maximum absorption wavelength of Compound 3 was used as the excitation wavelength and the light then emitted was observed and compared with the light emitted from the thin film of Compound 3 alone. The results are shown in Table 1.

Comparative Example 1

A thin film was formed and evaluated as in Example 2 with the exception of replacing Compound 3 with Alq3 as a host material. The results are shown in Table 1.

TABLE 1

| | Emission of light from host | Emission of light from dopant |
|---|---|---|
| Example 2 | X | ○ |
| Comparative example 1 | ○ | X |

When Compound 3 is used as a host material in the light-emitting layer, transition of energy occurs to Ir(ppy)3 and emission of light from Ir(ppy)3 is observed. When Alq3 is used instead, transition of energy does not occur to Ir(ppy)3 and Alq3 itself emits light.

Example 3

An organic EL device was fabricated as in FIG. 1 with omission of a hole-injecting layer and addition of an electron-injecting layer. Applying the vacuum deposition process at a degree of vacuum of 4.0×10⁻⁴ Pa, the constituent layers were stacked one upon another on a glass substrate having a 150 nm-thick ITO anode formed thereon. First, NPB was deposited on the ITO anode to a thickness of 60 nm to form a hole-transporting layer.

Next, Compound 3 and Ir(ppy)3 were co-deposited from different evaporation sources on the hole-transporting layer to a thickness of 25 nm to form a light-emitting layer. The concentration of Ir(ppy)3 at this point was 7.0 wt %. Then, Alq3 was deposited to a thickness of 50 nm to form an electron-transporting layer. Further, lithium fluoride (LiF) was deposited on the electron-transporting layer to a thickness of 0.5 nm to form an electron-injecting layer. Finally, aluminum (Al) as an electrode was deposited on the electron-injecting layer to a thickness of 170 nm to complete the fabrication of an organic EL device.

The organic EL device thus fabricated was connected to an outside power source and, upon application of direct current voltage, emission of light with the characteristics shown in Table 2 was confirmed. In Table 2, the luminance, voltage, and luminous efficiency are measured at 10 mA/cm². The maximum wavelength of the spectrum of light emitted from the device is 517 nm and this proves that light is emitted from Ir(ppy)3.

Comparative Example 2

An organic EL device was fabricated as in Example 3 with the exception of using HMTPD in the hole-transporting layer and TAZ as a host material in the light-emitting layer.

Comparative Example 3

An organic EL device was fabricated as in Example 3 with the exception of using TAZ as a host material in the light-emitting layer.

TABLE 2

| | Luminance (cd/m²) | Voltage (V) | Luminous efficiency (lm/W) |
|---|---|---|---|
| Example 3 | 2720 | 5.2 | 16.4 |
| Comparative Example 2 | 2050 | 13.2 | 4.9 |
| Comparative Example 3 | 1270 | 9.5 | 4.2 |

Example 4

(Synthesis of Compound 114)

In a 2000-ml three-necked flask that had been deaerated and filled with nitrogen were placed 50.69 g (0.2058 mole) of 3,3'-methylenediindole and 30.55 g (0.2061 mole) of triethyl orthoformate, then 640 g of methanol was added, and the mixture was stirred. To the mixture was added dropwise 5.0 g (0.0515 mole) of concentrated sulfuric over 3 minutes and the mixture was heated under reflux for 1 hour. The mixture was cooled to room temperature and the reddish brown crystals formed were collected by filtration and reslurried twice with 500 ml of methanol. The solvent was distilled off under reduced pressure and 36.81 g of solid C or indolo[3,2-b]carbazole (0.1438 mole, 69.9% yield) was obtained as a reddish brown powder.

Next, 4.36 g (100.0 mmoles) of a 55% dispersion of sodium hydride and 70 ml of dehydrated DMF were placed in a 2000-ml three-necked flask and the mixture was stirred in a stream of nitrogen. To this mixture was added dropwise a solution of 10.4 g (40.6 mmoles) of the aforementioned solid C in 150 ml of dehydrated DMF over 10 minutes. Upon completion of the dropwise addition, the mixture was stirred continuously for 1 hour. Then, to the mixture was added dropwise a solution of 20.9 g (78.0 mmoles) of 2-chloro-4,6-diphenyl-1,3,5-triazine in 300 ml of dehydrated over 1 hour. Upon completion of the dropwise addition, the mixture was stirred continuously for 3 hours. Thereafter, 900 g of water was added, the crystals separated were collected by filtration, reslurried twice with 450 g of water, further reslurried with 450 g of methanol, the solvent was distilled off under reduced pressure, and 42.0 g of brown crystals was obtained. The brown crystals were purified by crystallization from THF and methanol and stripped of the solvent under reduced pressure to give 13.4 g (18.6 mmoles, 46% yield) of a light brown solid or Compound 114: APCI-MS, m/z 719 [M+1]⁺; melting point, 498° C.

Example 5

(Synthesis of Compound 116)

In a 200-ml three-necked flask that had been deaerated and filled with nitrogen were placed 1.3 g (5.1 mmoles) of indolo

[3,2-b]carbazole, 1.4 g (14.6 mmoles) of sodium tert-butoxide, 8.2 mg (0.037 mmoles) of palladium acetate, 6.4 g (17.9 mmoles) of 2,6-diphenyl-4-iodopyridine, and 80 ml of xylene and the mixture was stirred at room temperature for 1 hour. To this mixture was added 64 mg (0.32 mmole) of tri-tert-butylphosphine and the resulting mixture was heated at 120° C. with stirring for 40 hours. The mixture was cooled to room temperature, 70 ml of water was added, and the precipitate was collected by filtration. The solid thus obtained was purified by reslurrying under heat successively with methanol, toluene, and chloroform to give 1.0 g (1.4 mmoles, 27.5% yield) of a pale brown solid or Compound 116: APCI-MS, m/z 715 [M+1]$^+$; melting point, 426° C.

Example 6

(Synthesis of Compound 2)

In a 1000-ml three-necked flask that had been deaerated and filled with nitrogen were placed 2.18 g (0.056 mole) of a 55% dispersion of sodium hydride and 240 ml of dehydrated DMF and the mixture was stirred in a stream of nitrogen. To this mixture was added dropwise a solution of 13.3 g (0.04 mole) of 11-phenylindolo[2,3-a]carbazole in 25 ml of dehydrated DMF over 10 minutes and thereafter the stirring was continued for 1 hour. Further, a solution of 8.8 g (0.048 mole) of 2,4,6-trichloro-1,3-pyrimidine in 150 ml of dehydrated DMF was added dropwise over 1 hour. Upon completion of the dropwise addition, the stirring was continued for 3 hours, then 500 ml of water was added, and the crystals separated were collected by filtration. The crystals were reslurried twice with 300 g of water and further reslurried with 300 g of methanol. The solvent was distilled off under reduced pressure and 18.2 g of light yellow crystals was obtained. The crystals were used in the next reaction without purification.

In a 2000-ml three-necked flask were then placed 18.2 g (0.038 mole) of the light yellow crystals obtained above, 9.73 g (0.08 mole) of phenylboronic acid, 1.84 g (0.0016 mole) of tetrakis(trisphenylphosphine)palladium, 150 ml of ethanol, and 450 ml of toluene and the mixture was stirred. To the mixture was added an aqueous solution of 29.8 g (0.28 mole) of sodium carbonate in 140 ml of water and the resulting mixture was heated at 85° C. with stirring for 4 hours. The mixture was cooled to room temperature, 200 ml of water and 200 ml of toluene were added, the mixture was separated into an organic layer and an aqueous layer, and the organic layer was washed with 200 ml of water. The organic layer was dehydrated over magnesium sulfate, the magnesium sulfate was filtered off, and the solvent was distilled off under reduced pressure. The residue was purified by crystallization from dichloromethane and ethanol, the solvent was distilled off under reduced pressure, and 5.2 g (0.0092 mole, 23% yield) of a white solid or Compound 2 was obtained: APCI-MS, m/z 563 [M+1]$^+$; melting point, 252° C.

Example 7

(Synthesis of Compound 29)

In a 100-ml three-necked flask were placed 0.21 g (0.94 mmole) of palladium(II) acetate, 20 ml of xylene, and 0.76 g (3.76 mmoles) of tri-tert-butylphosphine and the mixture was heated at 60° C. with stirring for 30 minutes. The resulting solution was sent into a solution that had been prepared by dissolving 4.61 g (0.0180 mole) of indolo[2,3-a]carbazole, 5.8 g (0.018 mole) of 4-carbazolylbromobenzene, and 7.7 g (0.080 mole) of sodium tert-butoxide in 180 ml of xylene and heated at 60° C. in a stream of nitrogen and the combined solution was heated up to 130° C. and kept at this temperature for 5 hours with stirring. The solution was cooled to room temperature, 200 ml of water was added, and the organic layer was separated and concentrated under reduced pressure to give a crude product. The crude product was purified by crystallization from dichloromethane and ethanol, the solvent was distilled off under reduced pressure, and 4.2 g (0.0084 mole, 47% yield) of 11-(4-carbazolylphenyl)indolo[2,3-a]carbazole was obtained.

Then, 0.42 g (0.0096 mole) of a 55% dispersion of sodium hydride and 10 ml of dehydrated DMF were placed in a 200-ml three-necked flask that had been deaerated and filled with nitrogen and the mixture was stirred in a stream of nitrogen. To this mixture was added dropwise a solution of 4.0 g (0.008 mole) of 11-(4-carbazolylphenyl)indolo[2,3-a]carbazole obtained above in 20 ml of dehydrated DMF over 10 minutes. Upon completion of the dropwise addition, the mixture was stirred for 1 hour or so and to this mixture was added dropwise a solution of 2.14 g (0.008 mole) of 2-chloro-4,6-diphenyl-1,3,5-triazine in 20 ml of dehydrated DMF over 1 hour. Upon completion of the dropwise addition, the mixture was stirred for 3 hours, 100 g of water was added, and the crystals separated were collected by filtration. The crystals were reslurried twice with 100 g of water, then reslurried with 100 g of methanol. The solvent was distilled off under reduced pressure and the residue was purified by crystallization from THF/methanol to give 3.0 g (0.0041 mole, 51% yield) of a yellow solid or Compound 29: APCI-MS, m/z 729 [M+1]$^+$; melting point, 319° C.

Example 8

(Synthesis of Compound 37)

In a 2000-ml three-necked flask that had been deaerated and filled with nitrogen were placed 4.80 g (110.0 mmoles) of a 55% dispersion of sodium hydride and 70 ml of dehydrated DMF and the mixture was stirred in a stream of nitrogen. To this mixture was added dropwise a solution of 13.5 g (52.7 mmoles) of indolo[2,3-a]carbazole in 150 ml of dehydrated DMF over 10 minutes. Upon completion of the dropwise addition, the mixture was stirred for 1 hour or so and to this mixture was added dropwise a solution of 29.4 g (110.0 mmoles) of 2-chloro-4,6-diphenyl-1,3,5-triazine in 150 ml of dehydrated DMF over 1 hour. Upon completion of the dropwise addition, the mixture was stirred for 3 hours, 900 g of water was added, and the crystals separated were collected by filtration. The crystals were reslurried twice with 450 g of water, further reslurried with 450 g of methanol, the solvent was distilled off under reduced pressure, and 35.0 g of crystals was obtained. Purification of the crystals by crystallization from THF/methanol gave 24 g (33.4 mmoles, 63.4% yield) of a yellow solid or Compound 37: APCI-MS, m/z 719 [M+1]$^+$; melting point, 426° C.

Example 9

(Synthesis of Compound 1)

In a 20-ml three-neck flask that had been deaerated and filled with nitrogen were placed 0.071 g (0.32 mmoles) of palladium(II) acetate, 5 ml of xylene, and 0.32 ml (1.26 mmoles) of tri-tert-butylphosphine and the mixture was heated at 60° C. with stirring for 30 minutes. The resulting solution was sent into a solution that had been prepared by dissolving 1.99 g (0.0060 mole) of 11-phenylindolo[2,3-a]carbazole, 2.46 g (0.0069 mole) of 2,6-diphenyl-4-iodopyridine, and 2.57 g (0.0267 mole) of sodium tert-butoxide in 60 ml of xylene and heated at 60° C. in a stream of nitrogen. The mixture was heated up to 130° C. and kept at this temperature for 5 hours with stirring. The mixture was cooled to room temperature, 70 ml of water was added, and the organic layer was separated and concentrated under reduced pressure to give 4.85 g of a crude product. The crude product was purified by crystallization from dichloromethane and ethanol, the solvent was distilled off under reduced pressure, and 1.43 g (0.0025 mole, 36% yield) of a white solid or Compound 1 was obtained: APCI-MS, m/z 562 [M+1]$^+$; melting point, 277° C., 287° C.

Example 10

An organic EL device was fabricated as in FIG. 1 with addition of an electron-injecting layer. Applying the vacuum deposition process at a degree of vacuum of $4.0\times10^{-4}$ Pa, the constituent layers in thin film were stacked one upon another on a glass substrate having formed thereon a 150 nm-thick ITO anode. First, copper phthalocyanine (CuPC) was deposited on the ITO anode to a thickness of 20 nm to form a hole-injecting layer. Then, NPB was deposited to a thickness of 40 nm to form a hole-transporting layer. Next, Compound 3 and Ir(ppy)3 were co-deposited on the hole-transporting layer from different evaporation sources to a thickness of 35 nm to form a light-emitting layer. The concentration of Ir(ppy)3 at this point was 7.0 wt %. Then, Alq3 was deposited to a thickness of 40 nm to form an electron-transporting layer. Further, lithium fluoride (LiF) was deposited on the electron-transporting layer to a thickness of 0.5 nm as an electron-injecting layer. Finally, aluminum (Al) was deposited as an electrode on the electron-injecting layer to a thickness of 170 nm to complete the fabrication of an organic EL device.

The organic EL device thus fabricated was connected to an outside power source and, upon application of direct current voltage, emission of light from the device with the characteristics shown in Table 3 was confirmed. The luminance, voltage, and luminous efficiency are measured at 10 mA/cm$^2$. The maximum wavelength of the spectrum of light emitted from the device is 517 nm and this proves that light is emitted from Ir(ppy)3.

An organic EL device was fabricated as in Example 10 with the exception of using Compound 114, 116, 2, 29, 37, or 1 as the main component of the light-emitting layer. The luminous characteristics are shown in Table 3. All the devices fabricated by using Compounds 114, 116, 2, 29, 37, and 1 that were respectively synthesized in Examples 4 to 8 were confirmed to emit light from Ir(ppy)3.

TABLE 3

| | Compound No | Luminance (cd/m$^2$) | Voltage (V) | Luminous efficiency (lm/W) |
|---|---|---|---|---|
| Example 10 | 3 | 2850 | 4.9 | 18.3 |
| Example 11 | 114 | 1970 | 6.1 | 10.1 |
| Example 12 | 116 | 3100 | 7.9 | 12.3 |
| Example 13 | 2 | 2900 | 5.5 | 16.6 |
| Example 14 | 29 | 3320 | 6.3 | 16.6 |
| Example 15 | 37 | 2280 | 6.5 | 11.0 |
| Example 16 | 1 | 2740 | 6.7 | 12.8 |

INDUSTRIAL APPLICABILITY

This invention enables an organic EL device to emit light of high luminance at high efficiency with application of low voltage. Accordingly, the organic EL device of this invention is applicable to flat panel displays (for example, office computers and wall-hanging television sets), vehicle display devices, mobile phone displays, light sources utilizing the characteristics of planar light emitters (for example, light sources of copying machines and backlight sources of liquid crystal displays and instruments), signboards, and beacon lights and has a high technical value.

The invention claimed is:

1. A compound for use in an organic electroluminescent device represented by the following general formulas (2)-(7):

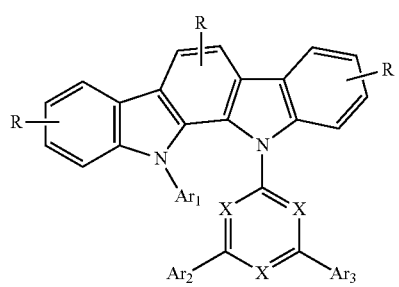

(2)

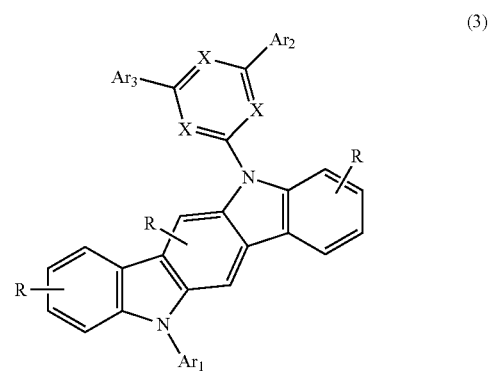

(3)

(4)

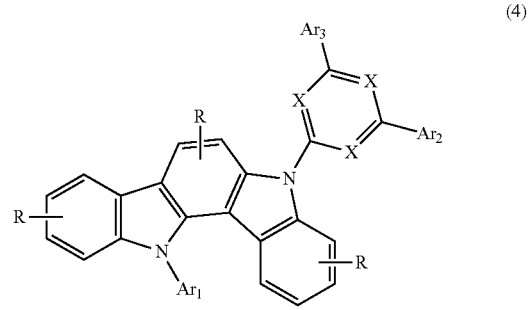

(5)

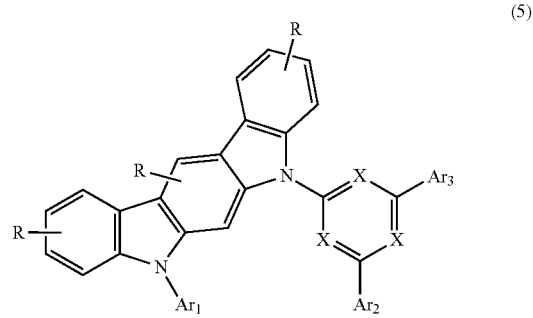

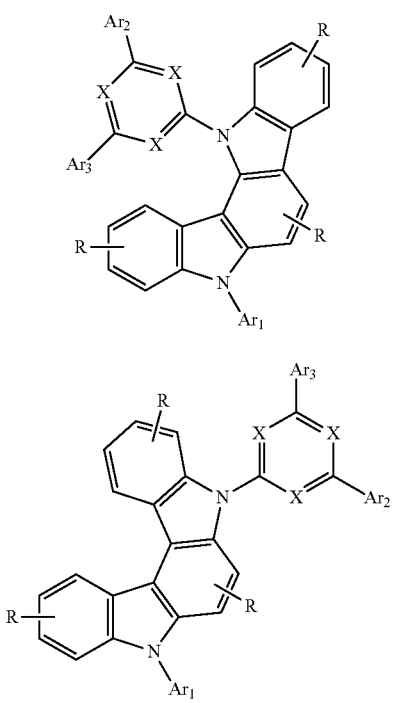

wherein:
X is CH or N and at least one of Xs is a nitrogen atom;
Ar$_1$ to Ar$_3$ each is independently a substituted or unsubstituted non-condensed aromatic hydrocarbon group or a substituted or unsubstituted non-condensed aromatic heterocyclic group and Ar$_2$ or Ar$_3$ may form a condensed ring with the X-containing ring;
R is hydrogen or a monovalent substituent.

2. A compound for use in an organic electroluminescent device as described in claim 1 wherein R in formulas (2)-(7) is independently hydrogen, an alkyl group, an aralkyl group, an alkenyl group, an alkynyl group, a cyano group, a dialkylamino group, a diarylamino group, a diaralkylamino group, an amino group, a nitro group, an acyl group, an alkoxycarbonyl group, a carboxyl group, an alkoxyl group, an alkylsulfonyl group, a haloalkyl group, a hydroxyl group, an amide group, a substituted or unsubstituted aromatic hydrocarbon group, or a substituted or unsubstituted aromatic heterocyclic group.

3. A compound for use in an organic electroluminescent device as described in claim 1 wherein R in formulas (2)-(7) is independently hydrogen, a substituted or unsubstituted aromatic hydrocarbon group of 5 to 18 carbon atoms, or a substituted or unsubstituted aromatic heterocyclic group of 3 to 17 carbon atoms.

4. A compound for use in an organic electroluminescent device as described in claim 1 wherein Ar$_1$ to Ar$_3$ each in formulas (2)-(7) is independently a substituted or unsubstituted phenyl group or a substituted or unsubstituted aromatic heterocyclic group of 2 to 5 carbon atoms.

5. A compound for use in an organic electroluminescent device as described in claim 1 wherein the said compound is represented by formula (2) or by formula (3).

6. An organic electroluminescent device which contains an organic layer comprising the compound for use in an organic electroluminescent device described in any one of claims 1 to 5.

7. An organic electroluminescent device as described in claim 6 wherein the organic layer comprising the compound for use in an organic electroluminescent device is at least one layer selected from a light-emitting layer, a hole-transporting layer, an electron-transporting layer, and a hole-blocking layer.

8. An organic electroluminescent device as described in claim 6 wherein the organic layer comprising the compound for use in an organic electroluminescent device is a light-emitting layer of the said device disposed between an anode and a cathode stacked one upon another on a substrate and the said light-emitting layer comprises a phosphorescent dopant and the said compound for use in an organic electroluminescent device as a host material.

9. An organic electroluminescent device as described in claim 8 wherein a hole-injecting/transporting layer is disposed between the anode and the light-emitting layer and an electron-injecting/transporting layer is disposed between the cathode and the light-emitting layer.

10. An organic electroluminescent device as described in claim 9 wherein the hole-blocking layer is disposed between the light-emitting layer and the electron-injecting/transporting layer.

* * * * *